United States Patent
Maretto et al.

(10) Patent No.: US 9,925,026 B2
(45) Date of Patent: Mar. 27, 2018

(54) ADAPTERS, TIPS, AND DENTAL ASSEMBLIES

(71) Applicant: Kerr Corporation, Orange, CA (US)

(72) Inventors: Emanuele Maretto, Mariano C.se (IT); Matteo Bosisio, Lugano (CH); Gopikrishnan Soundararajan, Aliso Viejo, CA (US); Mehdi Durali, Carlsbad, CA (US); Carlos Munoz, Orange, CA (US)

(73) Assignee: Kerr Corporation, Orange, CA (US)

( * ) Notice: Subject to any disclaimer, the term of this patent is extended or adjusted under 35 U.S.C. 154(b) by 0 days.

(21) Appl. No.: 14/801,140

(22) Filed: Jul. 16, 2015

(65) Prior Publication Data

US 2016/0015495 A1    Jan. 21, 2016

Related U.S. Application Data

(60) Provisional application No. 62/026,961, filed on Jul. 21, 2014.

(51) Int. Cl.
*A61C 5/04* (2006.01)
*A61C 19/06* (2006.01)
(Continued)

(52) U.S. Cl.
CPC .............. *A61C 19/063* (2013.01); *A61C 1/07* (2013.01); *A61C 5/62* (2017.02); *B05C 17/00593* (2013.01)

(58) Field of Classification Search
CPC ........... A61C 19/063; A61C 1/07; A61C 5/04; A61C 5/06; A61C 5/064; A61C 5/062; A61C 9/0026; B05C 17/00593
(Continued)

(56) References Cited

U.S. PATENT DOCUMENTS 3,421,222 A * 1/1969 Newman ................ A61C 5/062
433/226
3,730,394 A    5/1973 Woodson
(Continued)

FOREIGN PATENT DOCUMENTS

| DE | 10001513 A1 | 4/2001 |
| EP | 0480472 A2 | 4/1992 |
| EP | 2289457 A1 | 3/2011 |

OTHER PUBLICATIONS

European Patent Office, Search Report issued in Application No. EP 15 17 7745 dated Dec. 10, 2015.

*Primary Examiner* — Cris L Rodriguez
*Assistant Examiner* — Gwen M Demosky
(74) *Attorney, Agent, or Firm* — Wood Herron & Evans LLP

(57) ABSTRACT

An adapter for coupling a compule with a dental handpiece including a piston. The compule contains a dental material. The adapter includes a coupling portion that defines openings for attaching the adapter to the compule and for attaching the adapter to the dental handpiece. A plunger portion extends through one opening and engages the piston. A breakable tab connects the coupling portion and the plunger portion and breaks during dispensing of the material. The plunger portion is then movable relative to the coupling portion. A tip for use with the dental handpiece includes a housing that defines a chamber. A needle extends from the housing and defines a lumen having an opening from which the dental material is dispensed. A plunger slides within the chamber to push the dental material through the lumen and includes a rib that seals the plunger against the chamber during sliding movement of the plunger.

18 Claims, 26 Drawing Sheets

(51) Int. Cl.
  *A61C 1/07*  (2006.01)
  *A61C 5/62*  (2017.01)
  *B05C 17/005*  (2006.01)

(58) Field of Classification Search
  USPC .............. 433/80, 81, 89, 90, 102, 224;
    222/386–391, 566–574, 153.06, 541.6;
    604/110, 200, 232, 82, 87, 38, 218,
    604/220–222, 224, 228
  See application file for complete search history.

(56) References Cited

U.S. PATENT DOCUMENTS

| | | | | |
|---|---|---|---|---|
| 4,457,712 | A * | 7/1984 | Dragan | A61C 5/04 222/391 |
| 4,470,505 | A * | 9/1984 | Korwin | A61C 5/066 206/219 |
| 4,569,662 | A * | 2/1986 | Dragan | A61C 5/062 433/89 |
| 4,892,427 | A * | 1/1990 | Ford | A45D 34/042 222/391 |
| 5,244,933 | A | 9/1993 | Eidenbenz et al. | |
| 5,306,147 | A * | 4/1994 | Dragan | A61C 5/062 433/90 |
| 5,593,304 | A | 1/1997 | Ram | |
| 5,692,642 | A * | 12/1997 | Brattesani | B05C 17/01 221/199 |
| 5,743,431 | A * | 4/1998 | Brattesani | B05C 17/01 222/1 |
| 6,290,503 | B1 | 9/2001 | Lemon et al. | |
| 7,014,462 | B1 * | 3/2006 | Tilse | A61C 17/20 433/226 |
| 7,097,452 | B2 | 8/2006 | Friedman | |
| 7,766,656 | B1 | 8/2010 | Feine | |
| 8,047,841 | B2 | 11/2011 | Jefferies | |
| 8,469,707 | B2 | 6/2013 | Emde | |
| 8,770,973 | B2 | 7/2014 | Wagner | |
| 8,822,564 | B2 | 9/2014 | Drechsler | |
| 8,827,701 | B2 | 9/2014 | Mossle | |
| 8,926,323 | B2 | 1/2015 | Mossle | |
| 8,944,814 | B2 | 2/2015 | Mossle | |
| 2005/0201813 | A1 * | 9/2005 | Lee | A61C 5/06 401/128 |
| 2005/0282117 | A1 * | 12/2005 | Aravena | A61B 17/8816 433/224 |
| 2006/0063126 | A1 * | 3/2006 | Aloise | A61C 1/16 433/81 |
| 2008/0206706 | A1 | 8/2008 | Mossle | |
| 2009/0191505 | A1 * | 7/2009 | Clark | A61C 5/04 433/39 |
| 2009/0224004 | A1 * | 9/2009 | Muller | G01F 11/026 222/309 |
| 2009/0255953 | A1 * | 10/2009 | May | A45D 34/04 222/1 |
| 2010/0206904 | A1 * | 8/2010 | Staub | A61C 5/064 222/137 |
| 2010/0304322 | A1 | 12/2010 | Emde | |
| 2011/0056984 | A1 * | 3/2011 | Cheetham | A61C 5/064 222/135 |
| 2011/0143303 | A1 | 6/2011 | Kilcher et al. | |
| 2011/0143305 | A1 * | 6/2011 | Wagner | A61C 5/02 433/29 |
| 2011/0151403 | A1 * | 6/2011 | Pauser | A61C 9/0033 433/82 |
| 2011/0314623 | A1 * | 12/2011 | Jimenez | A46B 11/0024 15/167.1 |
| 2012/0028216 | A1 | 2/2012 | Mossle | |
| 2012/0094251 | A1 | 4/2012 | Mossle | |
| 2012/0104050 | A1 * | 5/2012 | Mossle | A61C 1/07 433/118 |
| 2012/0122054 | A1 | 5/2012 | Emde | |
| 2012/0295221 | A1 * | 11/2012 | Cheetham | A61C 5/064 433/90 |
| 2013/0183630 | A1 | 7/2013 | Krikorian et al. | |
| 2013/0216975 | A1 * | 8/2013 | Fritze | A61C 19/063 433/90 |
| 2013/0231673 | A1 * | 9/2013 | Vogt | A61C 5/064 606/93 |
| 2014/0011163 | A1 * | 1/2014 | Montgomery | A61C 19/063 433/217.1 |
| 2014/0252044 | A1 * | 9/2014 | Greter | B05C 17/00596 222/326 |
| 2015/0086940 | A1 | 3/2015 | Mossle | |

* cited by examiner

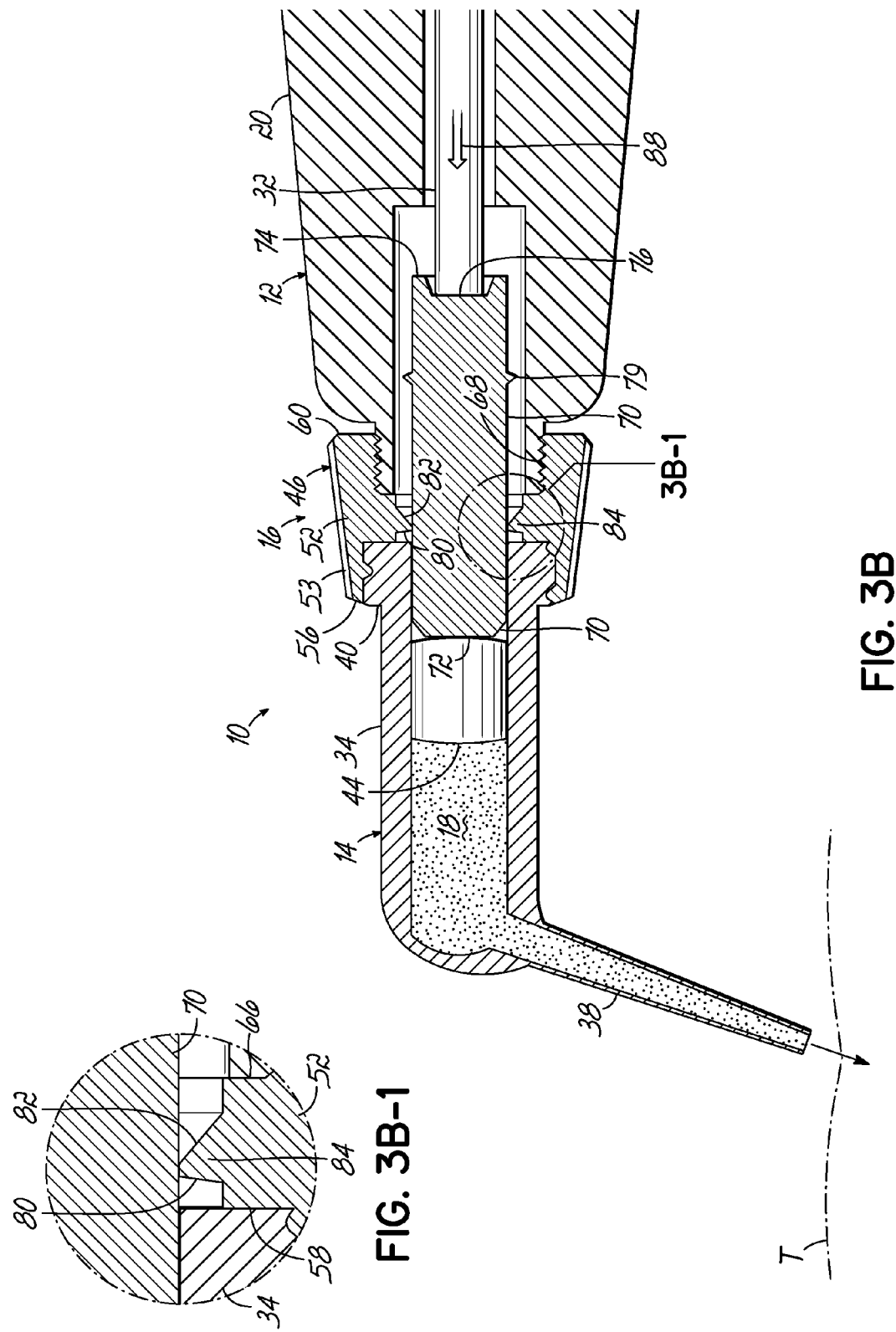

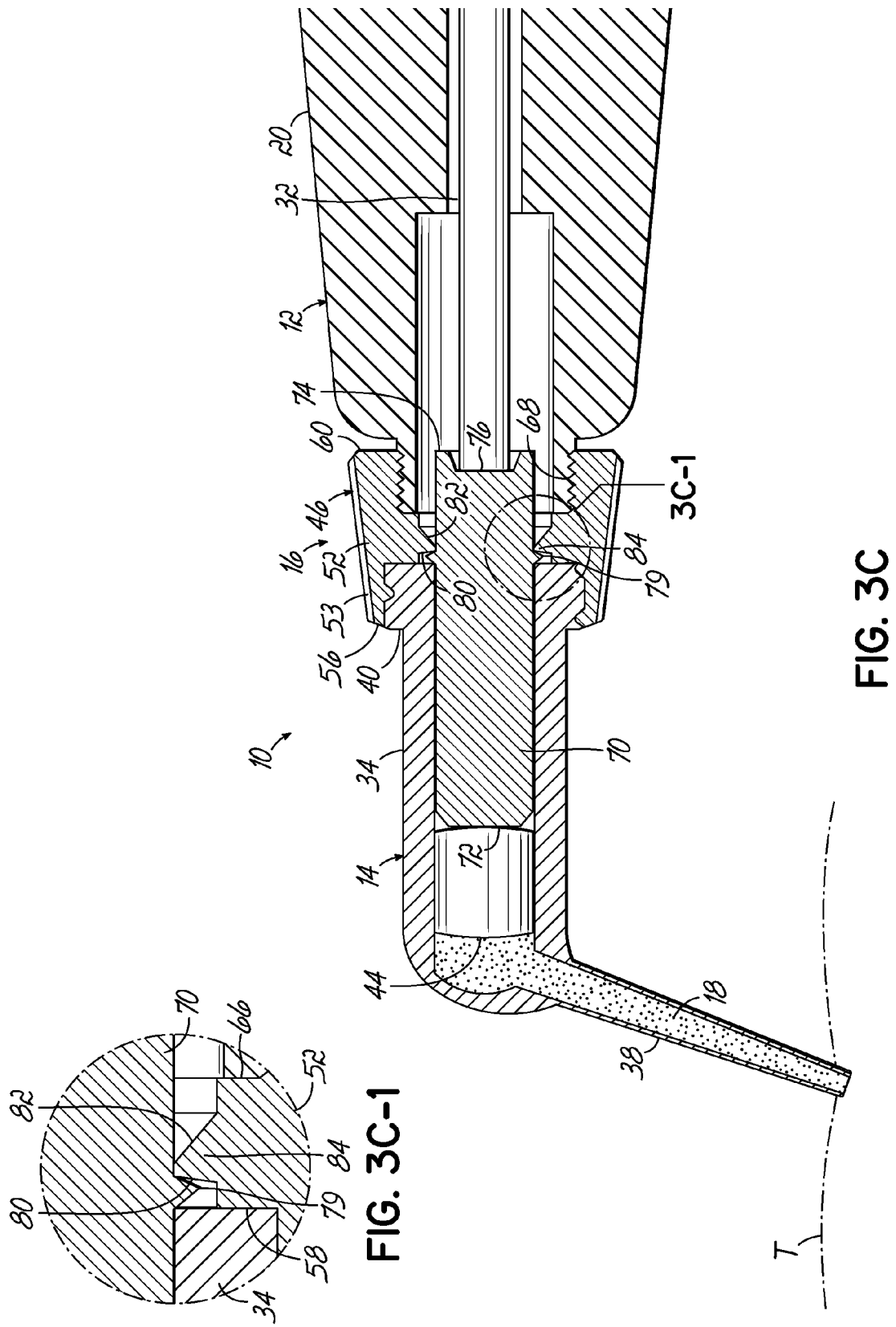

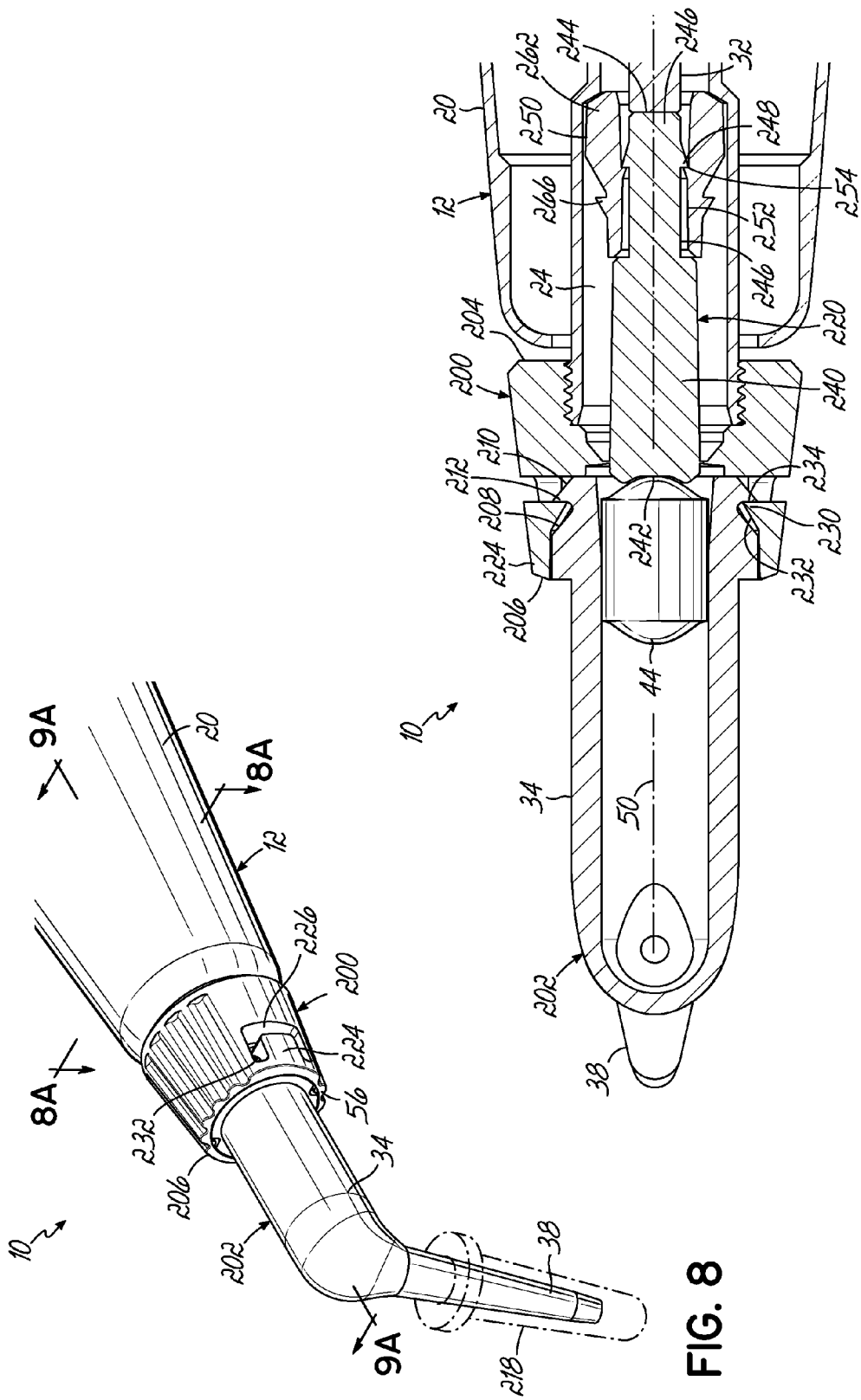

ADAPTERS, TIPS, AND DENTAL ASSEMBLIES

CROSS REFERENCE TO RELATED APPLICATIONS

This application claims priority to U.S. Provisional Patent Application Ser. No. 62/026,961, filed Jul. 21, 2014, the disclosure of which is incorporated by reference herein in its entirety.

TECHNICAL FIELD

The invention relates to adapters for use in dental treatment and, more particularly, adapters, tips, and dental assemblies for dispensing dental materials.

BACKGROUND

In dental technology, dental procedures may include gingival retraction in which a space is opened surrounding a preparation margin. Adequate retraction must be accomplished in all subgingival areas to guarantee that a dental impression material or digital scan registers at least the preparation margin. Different methods of gingival retraction may include the use of retraction cords, laser or electrosurgery, or retraction paste. During a retraction procedure with a retraction paste, the paste is dispensed or injected into the gingival sulcus. After a predetermined time, the paste is removed leaving a clean, dry and visible preparation margin. Once removed, the clinician may proceed with the impression or scan.

Dental procedures may also include restoration procedures. In this regard, the clinician may remove a defect, such as dead tissue, and then fill the cavity produced by removal of the defect with a filler material. Typically, curable materials are used to produce the filling. In this case, the filler material is placed in the cavity as a paste or liquid. Once the material cures, the filling seals the cavity. There are different types of fillings.

One type of filling is a direct restoration in which the filler material completely fills the cavity. Another type of filling is an indirect restoration in which a customized component, such as an inlay, is fabricated outside of the patient's mouth and is then inserted into the cavity. A filler material, for example, a dental cement, bonds the customized component with the wall of the cavity. The filler material mechanically anchors the component in the cavity, but also seals the cavity. In either case, the filling must not include gaps through which contaminants and germs may penetrate to potentially destroy the filling and damage the underlying tissue.

To that end, dispensing of the filler material into the cavity is particularly important to the successful formation of the filling. In the dental industry, a dental instrument may be used to dispense the filler material. The structural size and mechanical aspects of the instrument play a significant role in successfully dispensing the filler material into the cavity. The dental instrument may include a handpiece and a nozzle through which the filler material is dispensed into the cavity.

The handpiece may generate mechanical vibrations, such as, ultrasound, which may facilitate dispensing of the filler material through a nozzle. A combination of ultrasound and pressure make it possible to use filler masses with a relatively high content of fillers. These types of fillers may be preferred because of their relatively high toughness and resistance to shrinkage and to gap formation upon curing.

The nozzle may include a cartridge having a pre-selected formulation of filler material. The clinician may select a cartridge of or a nozzle containing a particular filler material for use. The nozzle/cartridge is secured to the handpiece in a manner that transmits the energy from the handpiece to the filler material. Upon actuation of the handpiece, the filler mass is dispensed from the nozzle into the cavity. Once dispensed, the filler material may return to a non-slumping, sculptureable state such that, before the filler material cures, the clinician may carve the filler material to match the patient's remaining anatomy.

While dental instruments and cartridges of specific formulations of filler material have been generally successful, manufacturers of such cartridges continually strive to improve their use and functionality. In this regard, there remains a need for broad cross application between handpieces and commercially available compules.

SUMMARY

The present invention overcomes the shortcomings and drawbacks of dental instruments and cartridges known for use in dispensing dental materials. While the invention will be described in connection with certain embodiments, it will be understood that the invention is not limited to these embodiments. On the contrary, the invention includes all alternatives, modifications and equivalents as may be included within the spirit and scope of the present invention. In accordance with the principles of the present invention, an adapter for coupling a compule (also referred to as a cartridge herein) with a dental handpiece includes a piston. The compule contains a dental material. The adapter comprises a coupling portion including a sidewall defining a first opening for attaching the adapter to the compule and a second opening for attaching the adapter to the dental handpiece. A plunger portion extends through the second opening of the coupling portion and engages the piston during dispensing of the dental material. A breakable tab connects the coupling portion and the plunger portion and is configured to break at a minimum predetermined load during dispensing of the dental material. When the breakable tab breaks, the plunger portion is movable relative to the coupling portion.

In one embodiment, the first opening is configured to prevent disassembly of the compule from the adapter once the compule is assembled with the adapter.

In one embodiment, the coupling portion and the plunger portion define a longitudinal axis of the adapter, and the first opening has a C-shaped configuration so that the compule is coupled to the adapter in a direction that is substantially perpendicular to the longitudinal axis. In one embodiment, the C-shaped configuration includes a first portion that defines a first transverse dimension and a second portion that defines a second transverse dimension. At least one of the first and second transverse dimensions is less than an outside dimension of the compule.

In one embodiment, the coupling portion includes a bendable tab that is configured to engage the compule.

In one embodiment, the first opening includes a snap-fit connection or a snap-on connection.

In one embodiment, during dispensing, the plunger portion locks the compule to the coupling portion.

In one embodiment, the sidewall includes a projection between the coupling portion and the plunger portion, and when the breakable tab breaks, the projection slidably engages the plunger portion during dispensing. In one embodiment, the projection forms a sliding seal with the plunger portion that substantially prevents contact between the dental material and the handpiece during dispensing.

In one embodiment, the breakable tab extends along an entire perimeter between the coupling portion and the plunger portion.

In one embodiment, the sidewall includes a projection and the breakable tab extends between the projection and the plunger portion.

In one embodiment, when the breakable tab breaks, the projection has a triangular shape.

In one embodiment, the plunger portion includes a ridge that engages the projection during dispensing to prevent the plunger portion from disengaging from the coupling portion at or near an end of dispensing of the dental material.

In one embodiment, the plunger portion includes a main body coupled to the coupling portion by the breakable tab and a sleeve that is slidable onto an end of the plunger portion and defines the ridge.

In one embodiment, the sleeve defines a skirt that is sized to slide in contact with the dental handpiece during dispensing of the dental material.

In one embodiment, the adapter further includes a shield member that is slidably received on the plunger portion and is configured to cooperate with the coupling portion during dispensing to substantially prevent the dental material passing between the plunger portion and the coupling portion from contacting the dental handpiece.

In one embodiment, the shield member includes a truncated cone-shaped bore defining a narrow dimension and a wide dimension and the shield member is positioned on the plunger portion such that the wide dimension is adjacent the coupling portion.

In one embodiment, at least a portion of the shield member is undersized relative to the plunger portion and is in an expanded state when positioned on the plunger portion prior to dispensing.

In accordance with another aspect of the present invention, a tip for use with a dental handpiece and which contains a dental material, comprises a housing that defines a chamber for containing the dental material. The tip further includes a needle that extends from the housing and that defines a lumen having an opening proximate a point from which the dental material is dispensed. A plunger is at least partially housed within the chamber and slides within the chamber to push the dental material through the lumen. The plunger includes a rib that seals the plunger against the chamber during sliding movement of the plunger.

In one embodiment, the rib substantially prevents the dental material from contacting the handpiece.

In one embodiment, the plunger further includes a second rib spaced apart from the rib, and the second rib forms a seal against the chamber during sliding movement of the plunger.

In one embodiment, the opening is oriented substantially perpendicularly to the lumen to dispense the dental material in a radial direction from the needle.

In one embodiment, the needle is deformable to one or more positions.

In accordance with another aspect of the present invention, a tip for use with a dental handpiece comprises a probe that transmits sonic energy from the dental handpiece to a tooth. The probe has a sleeve portion at one end and a point at the other end thereof. A hub couples the probe to the dental handpiece and includes a stud for engagement with the sleeve portion and a main body for engagement with the dental handpiece.

In one embodiment, the main body and the stud include a through bore that communicates with a receiving hole of the dental handpiece. The probe includes a vent that communicates with the through bore. The vent and the through bore relieve any pressure during assembly and use of the tip with the dental handpiece.

BRIEF DESCRIPTION OF THE DRAWINGS

The accompanying drawings, which are incorporated in and constitute a part of this specification, illustrate embodiments of the invention and together with the detailed description given below, serve to explain various aspects of the invention.

FIG. 3B is a cross-sectional view of the tip portion of the dental instrument shown in FIG. 1 depicting dispensing of a dental material;

FIG. 3B-1 is an enlarged view of the encircled area 3B-1 of FIG. 3B;

FIG. 3C is a cross-sectional view of the tip portion of the dental instrument shown in FIG. 1 nearing the completion of dispensing of the dental material;

FIG. 3C-1 is an enlarged view of the encircled area 3C-1 of FIG. 3C;

FIG. 8 is a perspective view of the dental instrument shown in FIG. 7;

FIG. 8A is a cross-sectional view of the dental instrument shown in FIG. 8 taken along section line 8A-8A;

DETAILED DESCRIPTION

Figure 1:
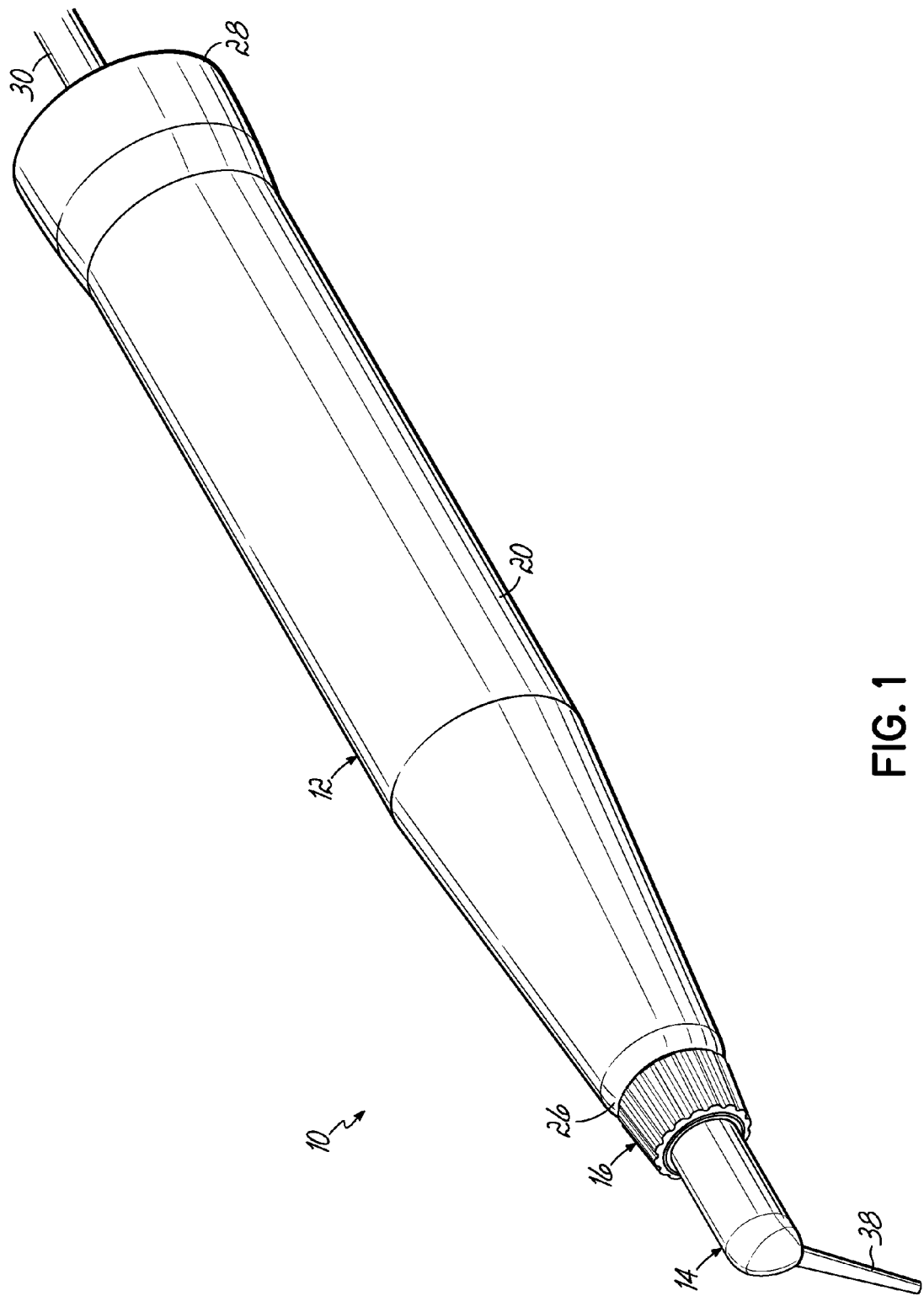
FIG. 1 is a perspective view of a dental instrument according to one embodiment of the invention.
Figure 2:
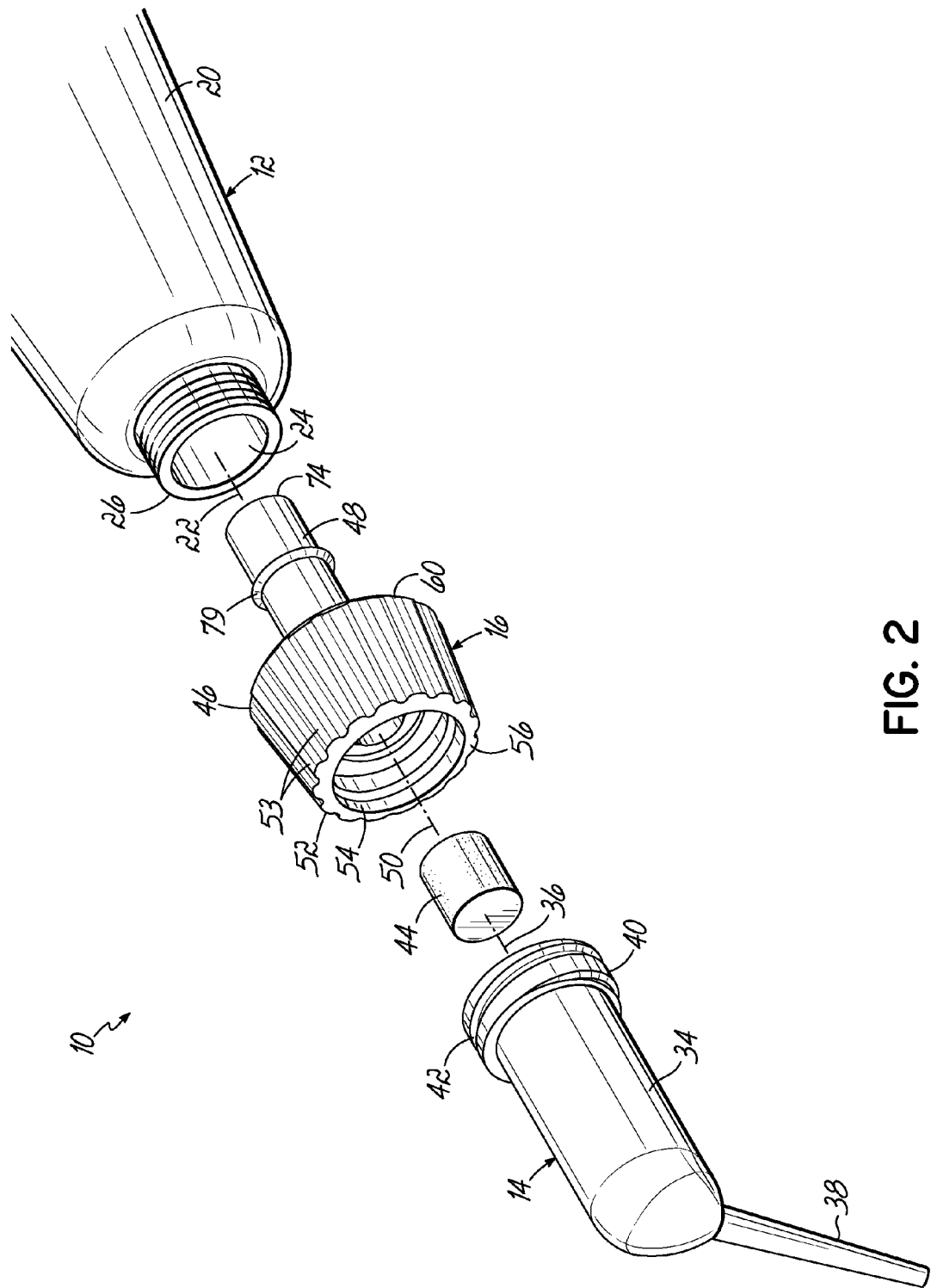
FIG. 2 is an exploded perspective view of a tip portion of the dental instrument shown in FIG. 1.
Figure 3A:
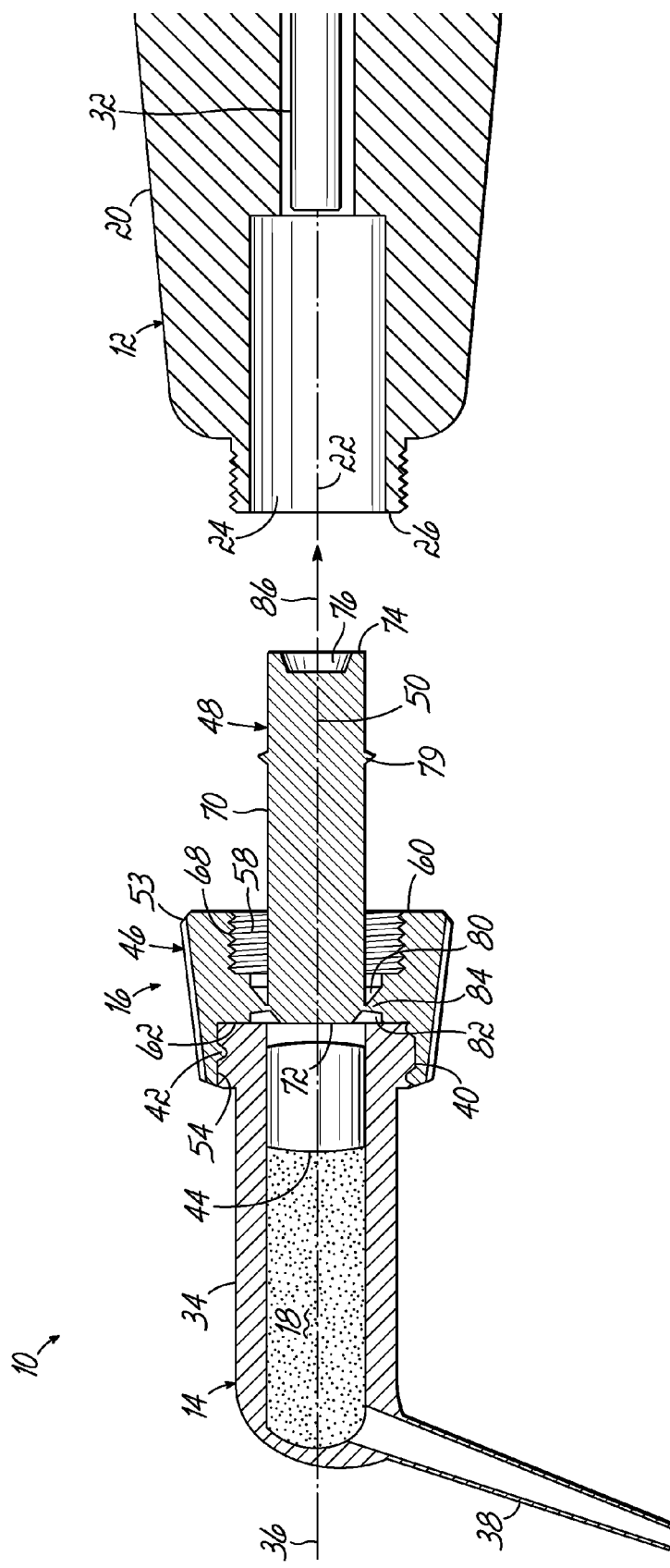
FIG. 3A is a disassembled cross-sectional view of the tip portion of the dental instrument shown in FIG. 1.

Referring now to the drawings, and to FIGS. 1, 2, and 3A in particular, in one embodiment of the invention, a dental instrument 10 may be used in a dental procedure, such as, a retraction procedure or a restoration procedure, for dispensing a dental material into a patient's mouth. To that end, in the embodiment shown in FIG. 1, the instrument 10 includes a hand apparatus, also referred to as a handpiece 12, that is coupled to a compule or cartridge 14 via an adapter 16. As will be described in detail below, the adapter 16 creates a mechanical connection between the handpiece 12 and the compule 14. According to embodiments of the invention, the adapter 16 permits use of a variety of compule configurations, as the compule configuration may vary by at least volume and dental material. As is known according to dental restoration procedures, the dental instrument 10 may be used to dispense a dental material 18 (FIG. 3B) proximate a tooth T. In this regard, as is known, preparation of a tooth during a restoration procedure may involve removing a damaged portion of the tooth with a dental bur and/or other instruments, which may leave a cavity or void in the tooth. To restore the mechanical integrity to the tooth, once the damaged portion of the tooth is removed, the dental material may be dispensed into the formed cavity.

To these and other ends, with reference to FIGS. 1, 2, and 3A, in general, the handpiece 12 may be configured to provide or generate energy by which the dental material 18 is selectively dispensed from the compule 14 proximate the tooth T. The handpiece 12 may include a shaft 20 having a longitudinal axis 22 and defining a receiving hole 24 at end 26. At opposing end 28, a flexible supply line 30 may be coupled to the handpiece 12 and supply pressurized gas from a gas source (not shown) in the clinician's office to the handpiece 12. The pressurized gas may ultimately be utilized to dispense the dental material 18 from the compule 14.

In that regard, and with reference to FIG. 3A, the handpiece 12 may house a piston 32 that is activated by pressurized gas supplied via the flexible supply line 30 (shown in FIG. 1). The piston 32 may cooperate with the adapter 16, as described below, to dispense the dental material 18 from the compule 14. The handpiece 12 may further provide vibrational energy, for example, ultrasonic energy, to the dental material 18 during dispensing thereof. In this regard, it is known that the viscosity of certain materials is reduced when exposed to ultrasound or other energy sources. Therefore, the combination of ultrasonic energy and pressure, for example, from the piston 32, may facilitate controlled dispensing of the dental material 18 from the compule 14. While embodiments of the invention are not particularly limited to a particular handpiece, exemplary handpieces are described in U.S. Pub. No. 2012/0094251, which is incorporated by reference herein in its entirety. Further, commercially available handpieces such as, the Sonicfill® handpiece available from Kerr Corporation, Orange, Calif., may be utilized according to embodiments of the present invention.

With reference to FIGS. 1, 2, and 3A, the compule 14 may have a dog leg shape defined by a main body portion 34 defining a longitudinal axis 36 and a tapered cannula 38 extending generally at an angle relative to the axis 36 proximate one end of the main body portion 34. A flange 40 may extend generally radially outwardly relative to the axis 36 from the main body portion 34. The flange 40 may include one or more features 42, such as a thread or a Luer-lock type connection, such as, Luer-Lok®, for coupling the compule 14 to the adapter 16. Other exemplary features 42 may include a snap-on type connection feature or a snap-fit type connection feature, each of which may not use threaded couplings for securing the adapter 16 and the compule 14. A single use type connector may also be suitable for use between the adapter 16 and the compule 14. This type of connection between the compule 14 and the adapter 16 may prevent their separation once initially coupled together. Advantageously, this type of connection may facilitate convenient disposal of a used compule and adapter combination and discourage reuse thereof.

As is shown in FIGS. 2 and 3A, the compule 14 may further include a piston 44 housed within the compule 14, in particular, in the main body portion 34. In use, the piston 44 contains the dental material 18 within the volume of the compule 14 and may be used to forcibly dispense the dental material 18 from the cannula 38. Compules that may be usable with the adapter 16 according to embodiments of the invention, include those that are usable with standard pneumatic syringes. The compule 14 may be pre-filled prior to its attachment to the adapter 16. In this regard, the compule 14 may be filled with the dental material 18 and capped with the piston 44 at a factory before delivery to the clinician's office. Although not shown, compules described herein may include a foil or membrane that separates the dental material from the cannula. The foil or membrane is ruptured during dispensing of the dental material. As is known, compules may be a one-time use component or consumable in the clinician's office. That is, once used in a restoration procedure, the at least partially emptied compule is disposed of or thrown away. By way of example only and not limitation, exemplary dental materials may include composites, cements, silicones, sealants, amalgams, and retraction paste, such as, Expasyl™ available from Pierre Rolland. It will be appreciated that the dental material may depend upon the type of procedure being performed.

Figure 2A:
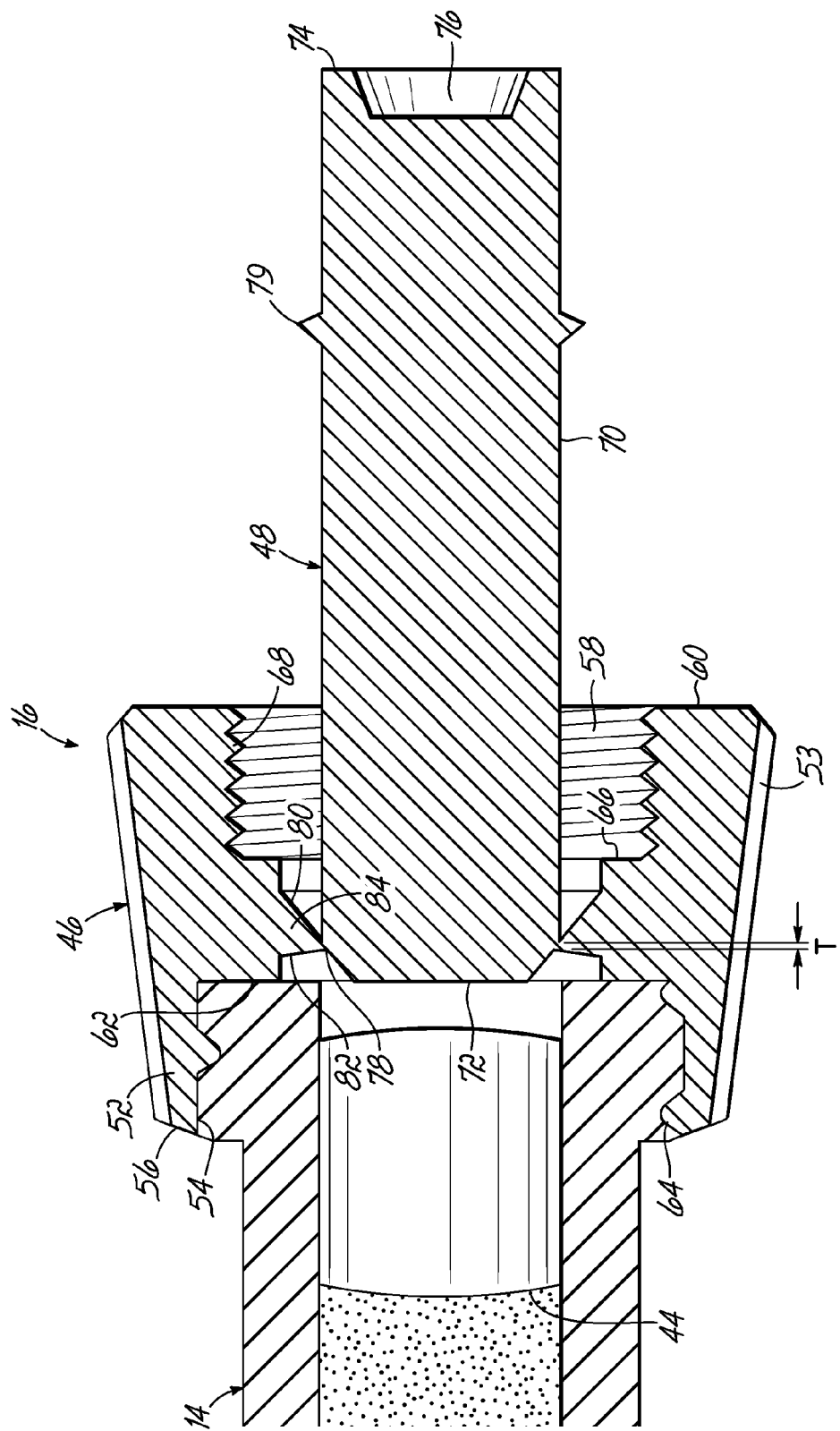
FIG. 2A is a cross-sectional view of an adapter shown in FIG. 1 according to one embodiment of the invention.

With reference to FIGS. 2 and 2A, in one embodiment, the adapter 16 has a coupling portion 46 and a plunger portion 48 that generally define a longitudinal axis 50 of the adapter 16. When assembled with the compule 14 and the handpiece 12, the coupling portion 46 is configured to secure the adapter 16 to each of the handpiece 12 and the compule 14, and the plunger portion 48 is configured to engage the piston 32 of the handpiece 12 and the piston 44 of the compule 14 during use, as is described below.

The coupling portion 46 includes a sidewall 52 having one or more ridges 53 to ease manual manipulation of the adapter 16 during assembly with the compule 14 and the handpiece 12. The sidewall 52 may be tapered relative to the axis 50 so as to provide a conical configuration to the coupling portion 46. It will, however, be appreciated that the sidewall 52 may have other configurations and embodiments of the present invention are not limited to the conical configuration shown in FIG. 2.

The sidewall 52 may define an opening 54 at one end 56 thereof. The opening 54 may extend only part way through the coupling portion 46 so that the sidewall 52 defines a bottom wall 62. The opening 54 may be dimensioned to cooperate with the flange 40 of the compule 14. In this regard, the opening 54 may include one or more features 64, such as, a thread (shown in FIG. 2A) that cooperates with the thread 42 on the compule 14 to secure the adapter 16 to the compule 14. Alternatively, the opening 54 may include single-use type connectors or snap-on or snap-fit connection features that cooperate with the compule 14. At the other end 60, the sidewall 52 may define an opening 58 that may also be of limited depth so that the sidewall 52 defines a bottom wall 66. The opening 58 may include one or more features 68 that cooperate with a feature, such as, a thread (as shown) on the end 26 of the handpiece 12.

With reference to FIGS. 2 and 2A, in one embodiment, the plunger portion 48 includes a plunger 70 in the configuration of a generally cylindrical body extending along the longitudinal axis 50 from within the opening 58 of the coupling portion 46. The plunger portion 48 includes a leading or front surface 72 and a trailing surface 74 disposed at the opposite end of the cylindrical body from the front surface 72. The front surface 72 is configured to cooperate with the piston 44 of the compule 14 and the trailing surface 74 includes a dimple or recess 76 that is sized to receive the piston 32 of the handpiece 12. The plunger 70 further includes a projection in the form of a circumferentially extending ridge 79 proximate the trailing surface 74.

The plunger portion 48 is connected to the coupling portion 46 by a breakable tab 78. The breakable tab 78 may extend between the plunger portion 48 and the coupling portion 46 around the entire perimeter of the plunger 70. That is, in the exemplary embodiment the breakable tab 78 may form a single continuous circumferential connection between the plunger 70 and the sidewall 52. However, it will be appreciated that embodiments of the present invention are not limited to a single continuous peripheral connection between the sidewall 52 and the plunger 70. For example, the breakable tab 78 may include more than one finite bridge between the sidewall 52 and the plunger 70 that are separated by one or more through slots or holes. By way of example only, there may be from 2 to 10 individual breakable tabs, and by way of further example, there may be up to 15 individual breakable tabs between the plunger 70 and the sidewall 52. In this regard, the breakable tab may have a perforated appearance.

In general, during use, the breakable tab 78 is configured to break at a predetermined load so that the plunger 70 separates from the coupling portion 46. The breakable tab 78 is a thin region or bridge of material between the coupling portion 46 and the plunger portion 48. In the exemplary embodiment, the tab 78 may be defined between opposing recesses 80, 82 that extend along the axis 50 from corresponding bottom walls 62, 66. The opposing recesses 80, 82 may define a triangular shaped projection 84 in the sidewall 52 that projects toward the axis 50. In the exemplary embodiment, the tab 78 may extend from the triangular shaped projection 84. While the tab 78 extends from a tapered region of the sidewall 52 (i.e., the projection 84), the tab 78 may extend directly, and without any taper, from the surface of the plunger 70. This configuration may ensure that failure of the tab 78 occurs near the surface of the plunger 70 so as to create a surface that is flush or nearly flush with the surrounding surface of the plunger 70 during use of the adapter 16.

The breakable tab 78 is configured to break at a predetermined load on the plunger portion 48. Thus, failure of the tab 78 is by design. More specifically, the breakable tab 78 may have a predetermined minimum threshold load at or above which the breakable tab 78 fails so as to allow the plunger 70 to separate from the coupling portion 46. This minimum load may be based on the load observed on the breakable tab 78 if the adapter 16 is unintentionally dropped prior to use. That is, the breakable tab 78 may be sufficiently strong so that it does not fail if the clinician drops the adapter 16 on the floor. By way of example only, the breakable tab 78 may be designed to survive a drop from 1 m above the floor. It will be appreciated that the load observed on the breakable tab 78 may depend on the material from which the adapter 16 is made and the overall dimensions of the adapter 16. By way of example only, and not limitation, the thickness T of the breakable tab 78 may be minimal and may measure from about 0.01 mm to about 0.5 mm and by way of further example may measure from about 0.05 mm to about 0.2 mm. The predetermined minimum threshold load at or above which the tab 78 is designed to fail may be in the range of about 3 newton (N) to about 300 N. By way of further example, the minimum threshold load at or above which a breakable tab is designed to fail may be within about 5 N to about 10 N each. The total load needed to break all the tabs may then be defined by the total number of tabs and the threshold load required to break each tab.

In one embodiment of the invention, prior to use, the adapter 16 is a monolithic piece of material, such as, a plastic. In other words, the plunger portion 48 and the coupling portion 46 are a single continuous piece of material. In this regard, the adapter 16 may be made by a single shot molding process, as is known in the art. A multi-shot molding process, for example, a two-shot molding process, may be used to manufacture the adapter 16 in a single operation of different materials. In this regard, each of the coupling portion 46 and the plunger portion 48 may be formed by separate shots during a multi-shot molding process. In particular, each of the coupling portion 46 and the plunger portion 48 may be formed of different materials in a single operation. It will be appreciated that the adapter 16 may be made by other methods known in the art and that embodiments of the present invention are not limited to any particular method of making the adapter 16. Further in this regard and while the embodiments of the invention are not limited to any particular material, the adapter 16 may be made of different types of plastic materials, such as, acrylonitrile butadiene styrene (ABS), polyoxymethylene (POM), high density polyethylene (PeHd), polypropylene (PP), Nylon 66, or other plastics or blends of compounds and with or without fiber reinforcement. Similarly, the compule 14 may be made of different types of plastic materials such as, ABS, POM, PeHd, PP, Nylon 66, or other plastics or blends of compounds and with or without fiber reinforcement.

During assembly of the compule 14 with the adapter 16, and with reference to FIGS. 2 and 3A, the axis 36 of the compule 14 may be aligned with the axis 50 of the adapter 16. The flange 40 of the compule 14 may be inserted into opening 54 of the coupling portion 46 and may contact the bottom wall 62 through relative rotation of the compule 14 and the adapter 16. In this orientation, the front surface 72 may be proximate the piston 44. The assembled compule 14 and adapter 16 may then be aligned with the axis 22 of the handpiece 12. Inserting the plunger portion 48 into the receiving hole 24 along the axis 22 of the handpiece 12 (as indicated by the arrow 86 in FIG. 3A) and manipulating the adapter 16 to securely engage the thread on the handpiece 12 with the thread within the opening 58 secures the adapter 16 to the handpiece 12. It will be appreciated that while the receiving hole 24 is shown having a thread, other configurations for securing the handpiece 12 to the adapter 16 are possible. For example, the opening 58 may be externally threaded or otherwise suitably structured for coupling to another dispensing device. Once assembled, the plunger 70 cooperates with the piston 32 at the recess 76.

With reference now to FIGS. 3B, 3B-1, 3C, and 3C-1, the instrument 10 may be brought into close proximity to a tooth T and the dental material 18 may be dispensed from the compule 14 by activating the energy source via the handpiece 12. At a predetermined threshold level of load, which may be a maximum of about 170 N, the breakable tab 78 fails. Failure of the tab 78 allows the plunger portion 48 to separate from the coupling portion 46.

Once the breakable tab 78 fails, the plunger 70 may be moved relative to the coupling portion 46. Specifically, the plunger 70 may then be pushed through the opening 54 relative to the coupling portion 46 to engage the piston 44. With further activation of the piston 32 in the direction of the arrow 88, together with any ultrasonic energy supplied by the handpiece 12, the plunger 70 is forced into the compule 14. The vibrational energy from the handpiece 12 is transmitted through the adapter 16 to the dental material 18. The dental material 18 is thereby forced from the main body portion 34 by driving the piston 32 into contact with the plunger 70 and is extruded out of the cannula 38 at the location on the tooth T designated by the clinician.

During continued dispensing of the dental material 18, the plunger 70 extends further into the volume of the main body portion 34 and the vibrational energy changes the viscosity of the dental material 18. In this regard, in one embodiment, the plunger 70 is matched in size and shape with the piston 44. It will be appreciated, however, that the piston 44 and the plunger 70 may not be the same size or the same shape.

As is shown in the enlarged view of FIG. 3B-1, in one embodiment, following failure of the breakable tab 78, the triangular shaped projection 84 may slidably cooperate with the exterior surface of the plunger 70. In the configuration in which the triangular shaped projection 84 extends circumferentially around the opening 54, the projection 84 may essentially seal the handpiece 12 from exposure to any dental material 18 that is squeezed backward between the piston 44 and the main body portion 34 during dispensing. In other words, the projection 84 may form a gasket-like seal between the coupling portion 46 and the plunger portion 48 during use. Advantageously, this configuration provides an additional seal between the handpiece 12 and the dental material 18 to ensure that the handpiece 12 is not contaminated with dental material 18. The dental material 18 can be corrosive when in contact with certain materials and/or stubbornly adhere to surfaces. Thus, the projection 84 may sealingly engage the plunger 70 so as to prevent contact between the dental material 18 and handpiece 12, which may prolong the useful lifetime of handpiece 12 by at least limiting corrosion of the handpiece 12, particularly the metal components, as well as reduce the time required to clean any residue of the dental material 18 from the handpiece 12. As is disclosed herein, embodiments of the adapter may advantageously form a barrier between the dental material and the handpiece and thus reduce or completely eliminate contact between the two. That is, no portion of the handpiece 12, including the piston 32, may come into contact with dental material. Another advantage may be that this configuration may provide a barrier between the handpiece 12 and the patient and thus reduce the risk of the patient being infected with an iatrogenic disease should the clinician fail to adequately disinfect the handpiece 12 between uses.

In one embodiment, as is shown in FIGS. 3C and 3C-1, as the piston 44 is pushed to near the end of the main body portion 34 proximate the cannula 38, the plunger 70 extends substantially into the main body portion 34 of the compule 14. At or near the end of the useful extension of the plunger 70 into the compule 14, the ridge 79 on the plunger 70 may contact the projection 84 of the sidewall 52. With sufficient additional load on the plunger 70, the ridge 79 may push through an opening defined by the projection 84. The ridge 79 may then contact the flange 40 of the compule 14 (see FIG. 3C-1), at which position the plunger 70 may no longer be movable relative to the compule 14. The interference between the ridge 79 and the flange 40 may guarantee the usage of all the available stroke of the piston 32 of the handpiece 12 while preventing over stroke of the piston 32. As a result, dispensing of the dental material 18 from the compule 14 comes to a stop. This may be a visual indication for the clinician that the compule 14 has been emptied. In addition, retraction of piston 32 into the handpiece 12 does not result in backwards movement of the plunger 70 as a result of any residual pressure in the compule 14 pushing backwards on the plunger 70. In this regard, the interference fit between the ridge 79 and the triangular shaped projection 84 stops backwards movement of the plunger 70 within the adapter 16.

In one embodiment, once the ridge 79 pushes through the opening defined by the projection 84, the plunger 70 couples the coupling portion 46 to the compule 14 in a manner that locks the compule 14 to the coupling portion 46 and the plunger 70. This may be the result of the ridge 79 engaging the compule 14 so as to lock the plunger 70 to the compule 14. As a result, the compule 14 may not be disassembled from the plunger 70 or the coupling portion 46 though the ridge 79 may support the compule 14 during its removal after use. In other words, where a thread is utilized, for example, the compule 14 may not be unscrewed from the coupling portion 46. However, the coupling portion 46 may be disconnected from the handpiece 12. Advantageously, this configuration may ensure a single use of each of the compule 14 and the adapter 16.

Once the clinician uses a desired amount of the dental material 18 from the compule 14 or the dental material 18 is substantially completely dispensed so as to push the ridge 79 through the opening defined by the triangular shaped projection 84, the clinician can disconnect the assembly of the compule 14 and the adapter 16 from the handpiece 12. The used compule and adapter may be then be disposed of. A new compule and adapter may be assembled with the handpiece 12 and the dental material within the new compule may be dispensed substantially the same as described in the previous paragraphs.

Figure 4:
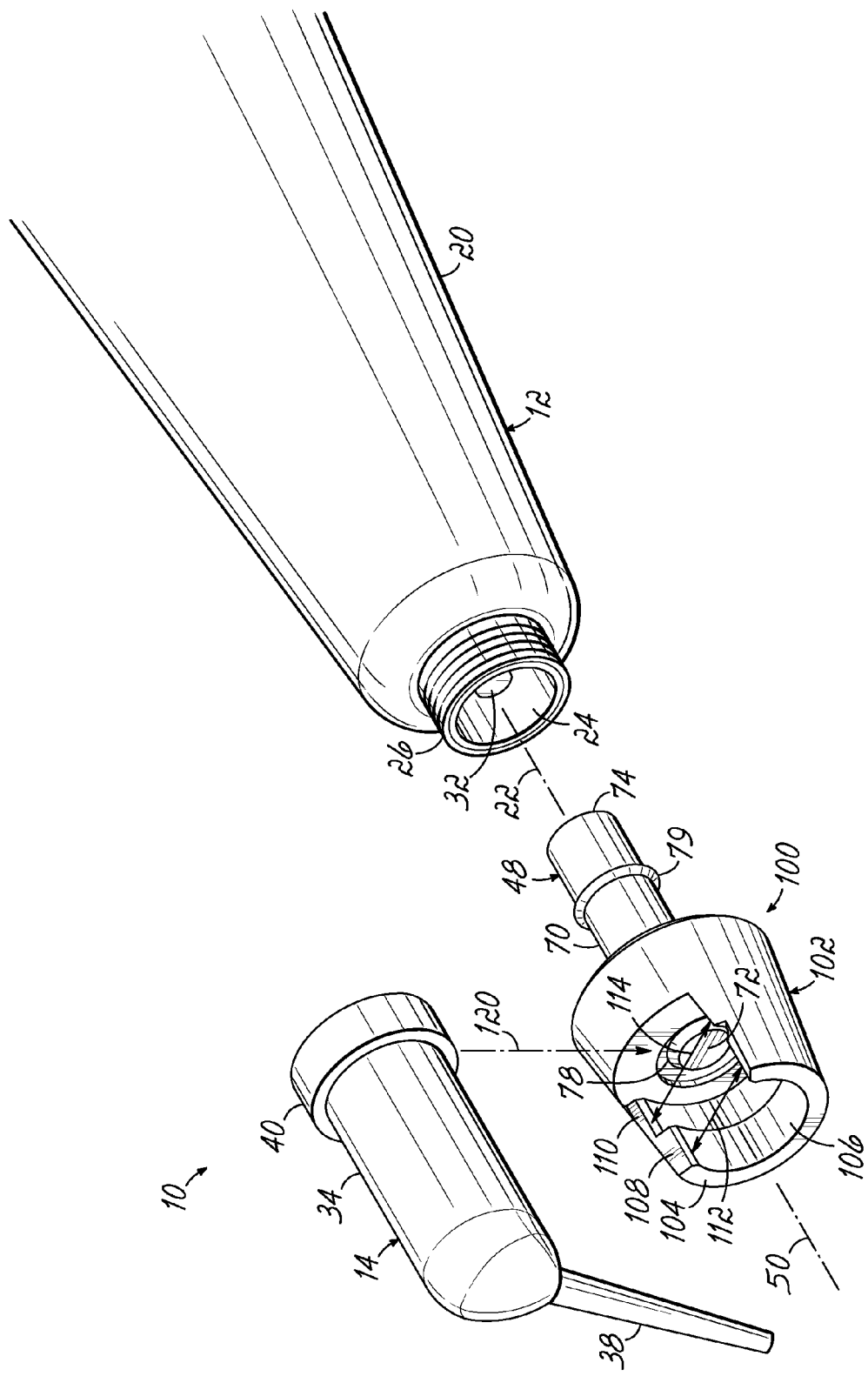
FIG. 4 is a disassembled perspective view of a tip portion of a dental instrument according to one embodiment of the invention.

With reference now to FIGS. 4-6B in which like reference numerals refer to like features in FIGS. 1-3C and in accordance with an embodiment of the invention, an adapter 100 may have a coupling portion 102 in which a sidewall 104 may only extend partially around the circumference of the coupling portion 102. As shown in FIG. 4, the sidewall 104 may form a generally C-shaped opening 106 that is configured to receive the compule 14 having a T-shape flange 40. In particular, the C-shaped opening 106 may include portions 108, 110 that define transverse dimensions 112, 114, respectively between opposing terminal ends of the portions 108, 110, as shown.

Figure 5:
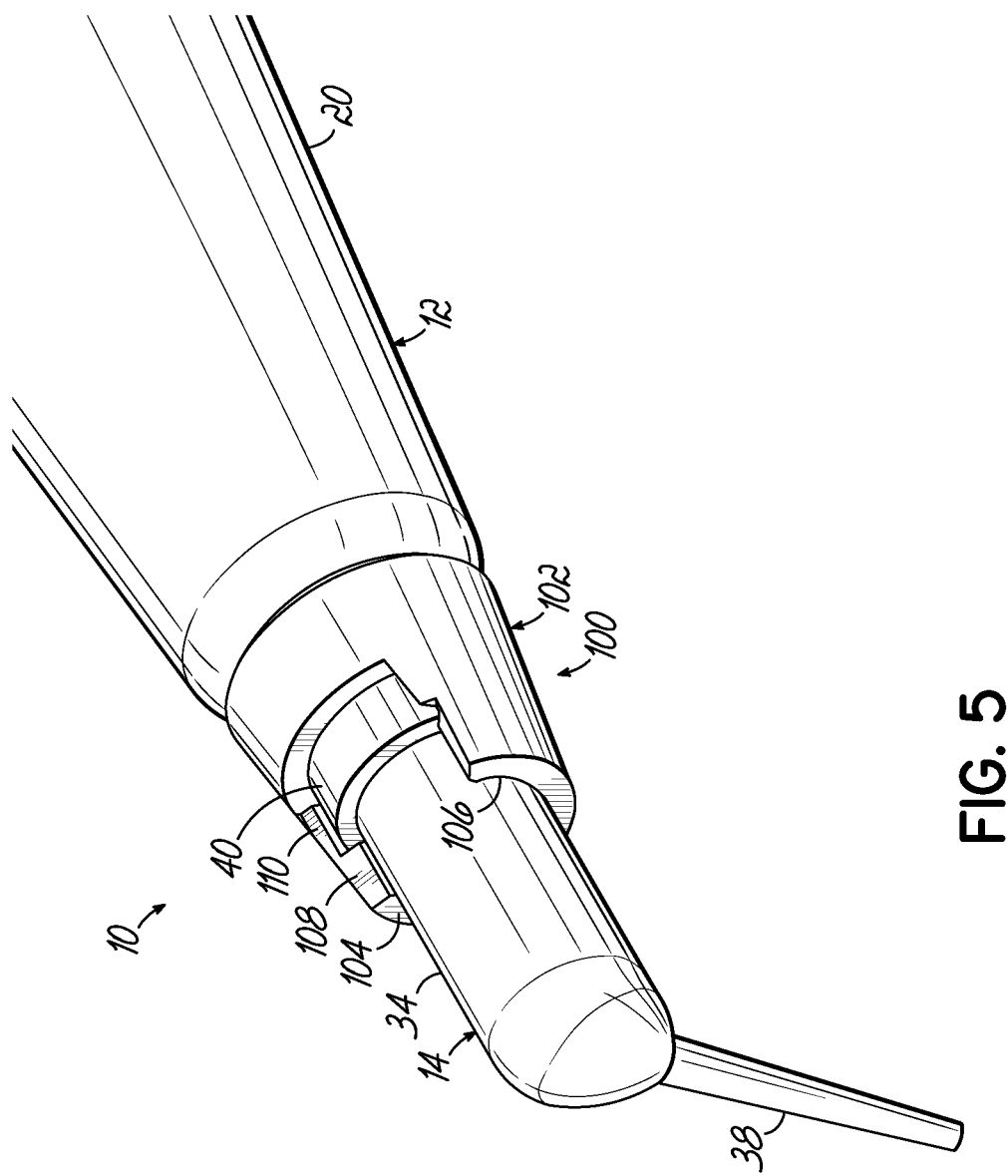
FIG. 5 is an assembled perspective view of the tip portion of the dental instrument shown in FIG. 4.

In one embodiment, the transverse dimension 112 and the transverse dimension 114 are less than the outside diameter of the main body portion 34 and the outside diameter of the flange 40, respectively, of the compule 14. As a result, insertion of the compule 14 into the adapter 100 may be accomplished in a direction that is generally perpendicular to the axis 50 of the adapter 100, as is indicated by arrow 120. Insertion may also require forcing the compule 14 through the C-shaped opening 106 due to the interference fit between the compule 14 and the C-shaped opening 106. The adapter 100 may be elastic such that upon a given amount of manually applied load the sidewall 104 expands at or near each of the portions 108, 110 to allow the compule 14 to snap into the adapter 100, as is shown in FIG. 5. Once inserted into the adapter 100, compule 14 is held in place along its longitudinal axis by the interference fit between the flange 40 and the portion 108 of the sidewall 104.

Figure 6A:
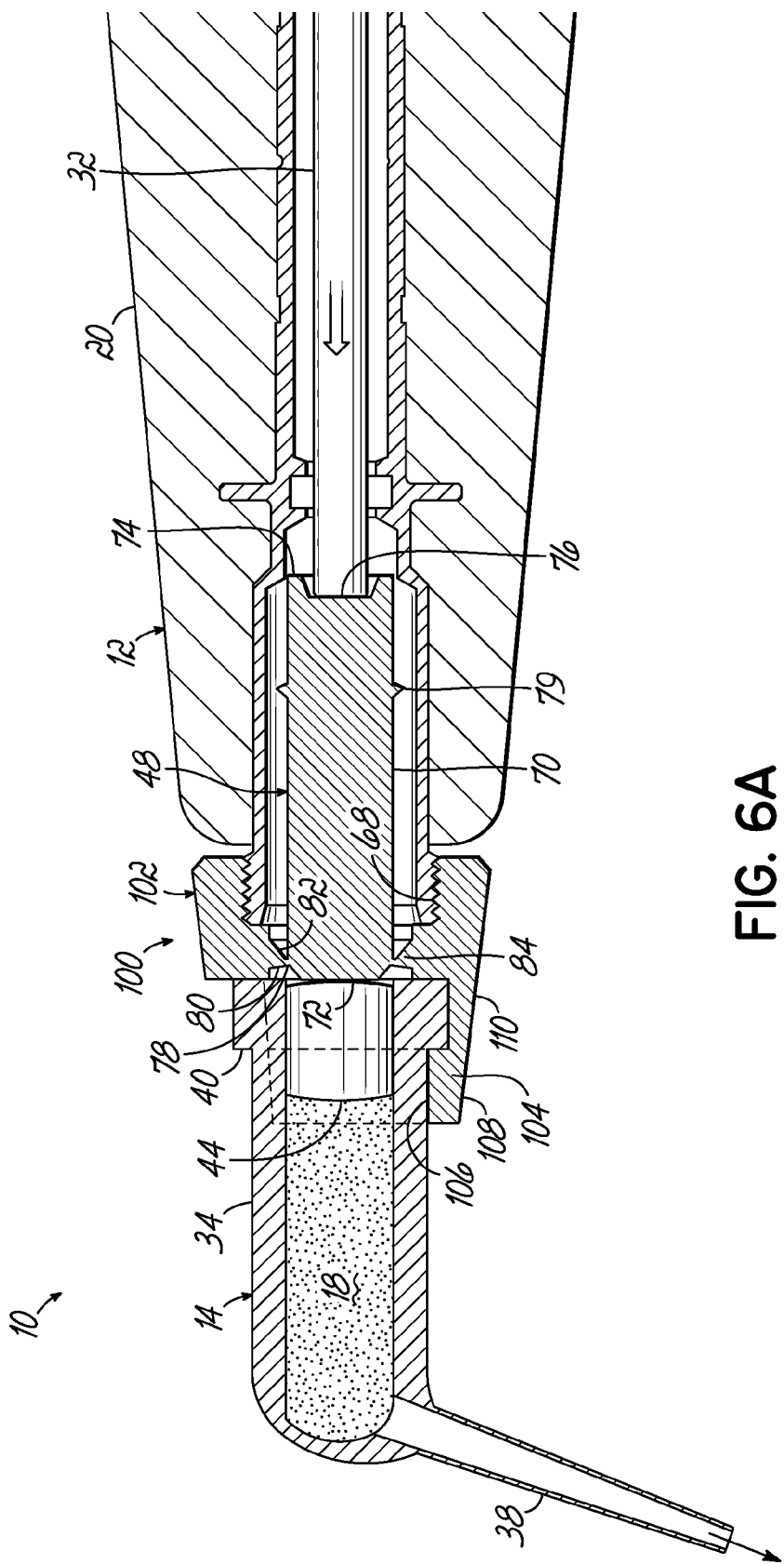
FIG. 6A is a cross-sectional view of the tip portion of the dental instrument shown in FIG. 5 prior to dispensing of a dental material.
Figure 6B:
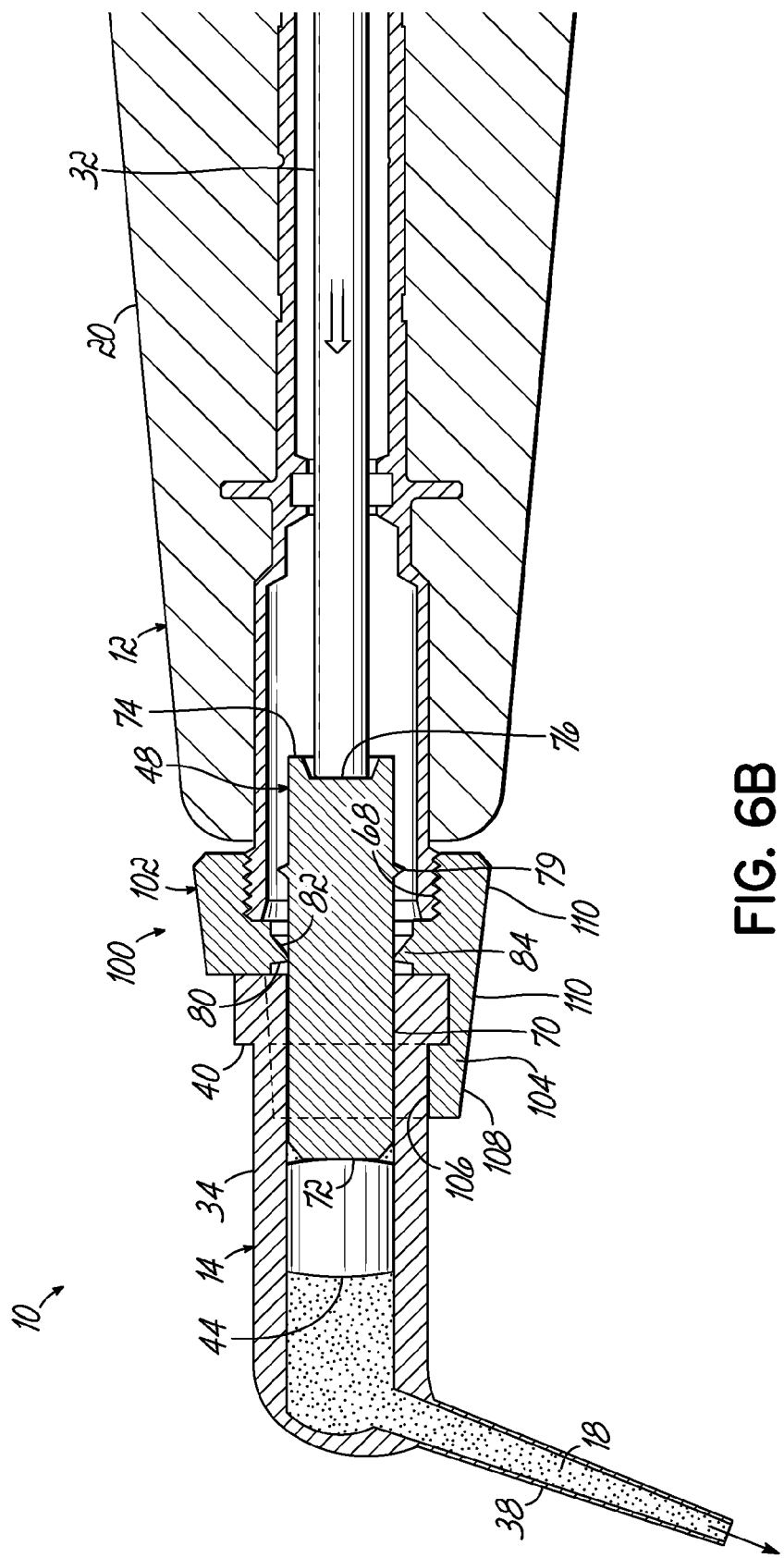
FIG. 6B is a cross-sectional view of the tip portion of the dental instrument shown in FIG. 5 during dispensing of the dental material.

Once assembled, and with reference now to FIGS. 6A and 6B, in one embodiment, the dental material 18 may be dispensed in a substantially similar way as described above with reference to FIGS. 3B and 3C. Briefly in this regard, activation of the piston 32 may forcibly engage the plunger 70 of the adapter 100. At a predetermined load on the plunger 70, the breakable tab 78 fails. This separates the coupling portion 102 of the adapter 100 from the plunger portion 48. Following separation, the plunger 70 forcibly contacts the piston 44 within the compule 14.

Further activation of the piston 32 together with any ultrasonic or other energy source in or through the handpiece 12, may drive the piston 32 and thus the plunger 70 forward, as shown in FIG. 6B. Movement of the plunger 70 pushes the piston 44 deeper into the main body portion 34 of the compule 14. This movement extrudes the dental material 18 from the cannula 38 at the location determined by the clinician. Although not shown, it will be appreciated that continued extension of the piston 32 may cause the ridge 79 to contact projection 84, as may be inferred from FIG. 6B. Further forcible extension of the piston 32 may push the ridge 79 through the opening defined by the triangular shaped projection 84 at which point dispensing of the dental material 18 may be at or near an end.

Figure 7:
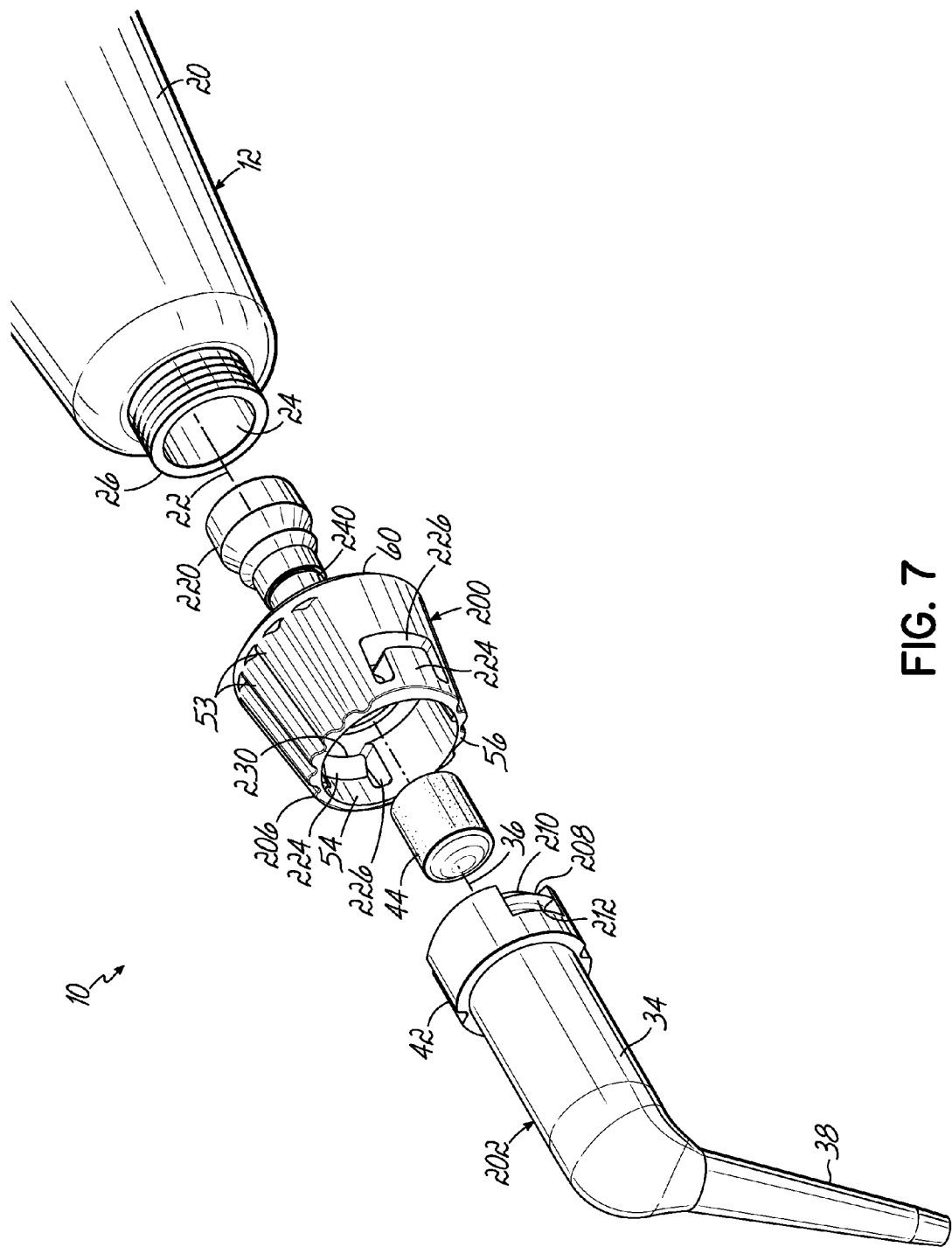
FIG. 7 is an exploded perspective view of a dental instrument according to one embodiment of the invention.

With reference now to FIGS. 7-9D in which like reference numerals refer to like features in FIGS. 1-3C and in accordance with one embodiment of the invention, the dental instrument 10 may include an adapter 200 that couples a cartridge 202 to the handpiece 12. As is shown in FIG. 7, the cartridge 202 may differ from the compule 14 shown in FIG. 2. In particular, the cartridge 202 may include the feature 42 in the configuration of a recessed wedge 208 that has a sawtoothed configuration. As shown, the wedge 208 may be formed in opposing sides of the feature 42. Each wedge 208 includes a ramp 210 and a stop 212, each of which cooperates with a portion of the adapter 200, described below, to lock the adapter 200 and the cartridge 202 together once assembled. Though locked together, in one embodiment, the cartridge 202 may be rotated plus or minus 25 degrees relative to the adapter 200 once assembled. A removable cap 218 (shown in phantom line in FIG. 8) fits over the cannula 38 and prevents damage and/or contamination of the cannula 38 prior to use. The compule 202 contains the dental material 18 and the piston 44 as described above with reference to FIG. 2, for example. The clinician may then remove the cap 218 to extrude the dental material 18. Similar to that described above, in one embodiment, the compule 202 is a one-time use component or consumable in the clinician's office and is disposed of or thrown away following use.

The adapter 200 may have a coupling portion 204 defined by a sidewall 206 that may extend around a circumference of the coupling portion 204 to define the opening 54. The coupling portion 204 is configured to secure the adapter 200 to each of the handpiece 12 and the compule 202. The adapter 200 further includes a plunger portion 220 that is received in the receiving hole 24 of the handpiece 12 to engage the piston 32 (FIG. 8A) of the handpiece 12 and the piston 44 of the compule 202 during use, as is described below. In this regard, the plunger portion 220 is sandwiched between the pistons 32 and 44.

With reference to FIG. 7, in particular, the sidewall 206 has one or more ridges 53 and may have a configuration similar to the adapter 16 described above with reference to FIG. 1 in other respects. In the exemplary embodiment shown, the sidewall 206 may have a conical configuration and may include a bendable tab 224. An opening 226 extends through the sidewall 206 and defines a portion of the bendable tab 224. The bendable tab 224 may flex relative to the sidewall 206 in a direction generally perpendicular to the axis 50. As shown, two bendable tabs 224 may correspond to the two recessed wedges 208. Each bendable tab 224 may include a projection 230 facing toward the longitudinal axis 50. With reference to FIG. 8A, the projection 230 has a tapered surface 232 and a stop surface 234. The tapered surface 232 is oriented in a manner similar to the ramp 210 of the wedge 208. For example, as shown, the ramp 210 is oriented in a direction that intersects the axis 50. This orientation positions the tapered surface 232 so as to cooperate with the ramp 210 during insertion of the cartridge 202 into the adapter 200.

In particular, during insertion and with reference to FIGS. 7 and 8A, when the compule 202 is inserted into the adapter along the axis 50, the ramp 210 engages the tapered surface 232. Although not shown, forcible engagement between the tapered surface 232 and the ramp 210 has a wedge-like effect and pushes the bendable tab 224 away from the axis 50. In this manner, with the application of additional force on the compule 202, the projection 230 passes over the recessed wedge 208. Once the bendable tab 224 clears the stop 212 as the cartridge 202 is pushed deeper into the opening 54, the bendable tab 224 springs back toward its original position (i.e., toward the axis 50). The stop surface 234 of the bendable tab 224 then faces the stop 212 of the recessed wedge 208. In this orientation (shown best in FIG. 8A), the bendable tab 224 and recessed wedge 208 cooperate to provide a one-way connection. The projection 230 interferes with the wedge 208 when the cartridge 202 is pulled in a direction away from the adapter 200 along axis 50. Thus, once the cartridge 202 is inserted into the adapter 200, they are coupled together so as to resist their separation.

Figure 9A:
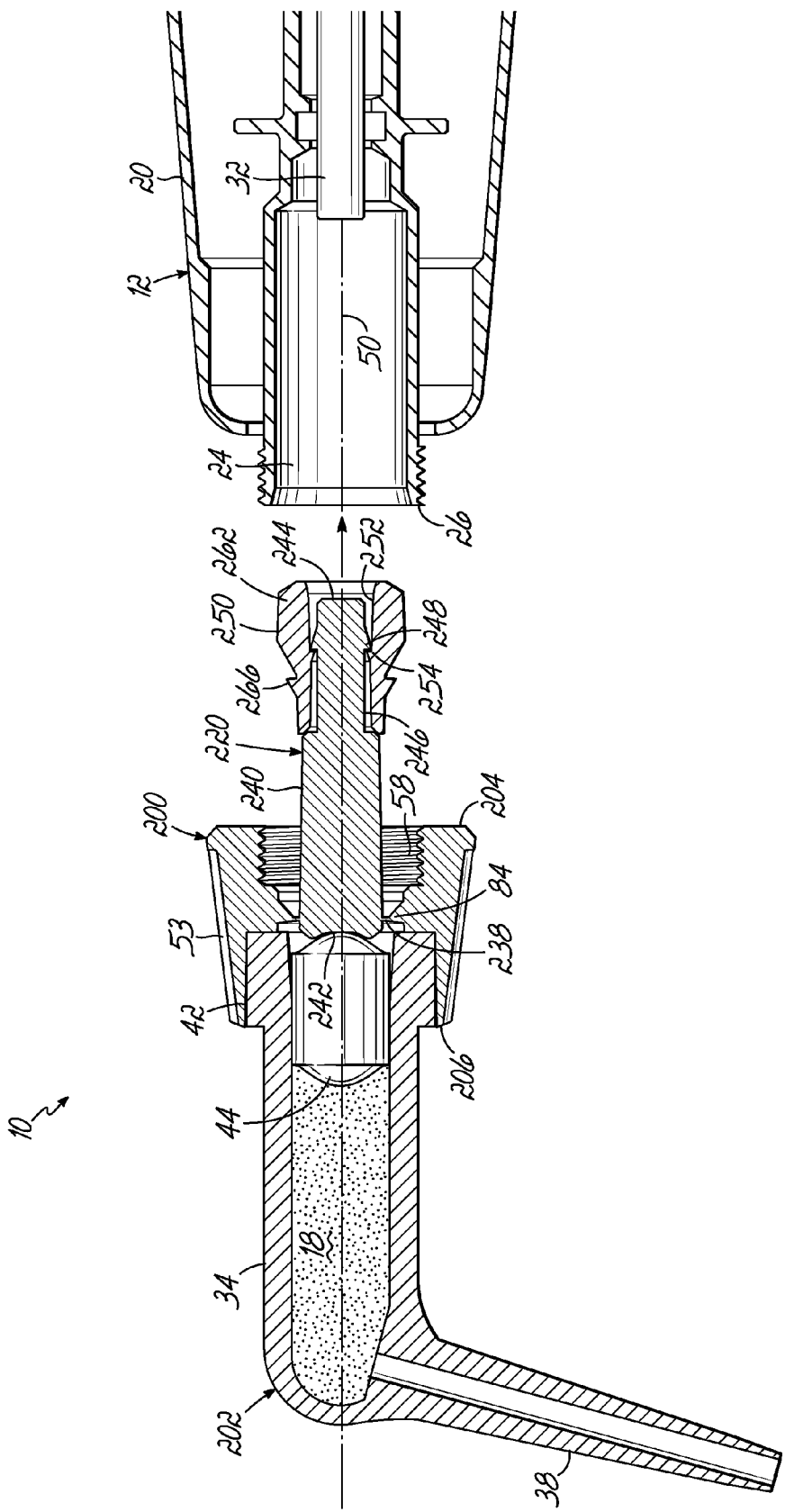
FIG. 9A is a cross-sectional view of the dental instrument shown in FIG. 8 taken along section line 9A-9A.

With reference to FIGS. 7, 8A, and 9A, in one embodiment, the plunger portion 220 is an assembly of two components. The first component includes a main body 240 and is similar to the plunger 70 described above with reference to FIG. 2A. In this regard, the main body 240 is coupled to the sidewall 206 at a breakable tab 238 (FIG. 9A). The breakable tab 238 operates in a similar manner as the breakable tab 78, described above. The main body 240 may be a generally cylindrical body extending along the longitudinal axis 50 from within the opening 58 of the coupling portion 204. The main body 240 includes a leading or front surface 242 and a trailing surface 244. The front surface 242 is configured to cooperate with the piston 44 of the compule 202, and the trailing surface 244 cooperates with the piston 32 of the handpiece 12 to transfer movement of the piston 32 to the piston 44. An extension 246, shown with a reduced diameter relative to the main body 240, extends from the main body 240 and defines the trailing surface 244 and includes a ridge 248 that cooperates with a second part of the plunger portion 220.

In the exemplary embodiment shown, the second part is a sleeve 250, which is sized to slide over the extension 246. The sleeve 250 may protect the plunger portion 220 during packaging and during partial use. In that regard, the sleeve 250 defines an inner surface 252, which includes an annular ridge 254 (FIG. 8A). The sleeve 250 is assembled with the extension 246 by slidably engaging the inner surface 252 with the extension 246. In particular, the ridge 248 engages the annular ridge 254 when properly assembled. In one configuration, the engagement between the ridge 248 and the ridge 254 is a one-way engagement. In this way, the sleeve 250 resists being detached from the plunger portion 220 once the ridge 248 engages the ridge 254.

In the embodiment shown in FIG. 9A, the sleeve 250 has an outer dimension that is larger than the outer dimension of the plunger 220. In one embodiment, the outer dimension of the sleeve 250 is approximately the size of the inside dimension of the receiving hole 24 of the handpiece 12. A portion of the sleeve 250 may therefore contact the inside of the receiving hole 24 and so slide in contact with the handpiece during dispensing of the dental material 18.

In this regard, the sleeve 250 may include a skirt 262 that surrounds the extension 246 and may extend past the trailing surface 244 of the main body 240 to form a pocket that is sized to cooperate with the piston 32. The skirt 262 may define an outer diameter that is slightly smaller than the inside diameter of the receiving hole 24. The skirt 262 therefore slidably engages the surfaces of the handpiece 12 and scrapes those surfaces as the piston 32 drives the plunger 220 forward to dispense the dental material 18. Scraping the skirt 262 along the walls defining the receiving hole 24 may remove any foreign materials that may be adhered to them. It will be appreciated that this function of the skirt 262 may promote the cleanliness of the handpiece 12.

The sleeve 250 may also define a ridge 266, much like the ridge 79 shown in FIG. 2 and described above. The ridge 266 may project outwardly but may not project as far as the skirt 262. Because of the outwardly projecting nature of the ridge 266, it may engage the projection 84 during dispensing of the dental material 18, as is described above.

Figure 9B:
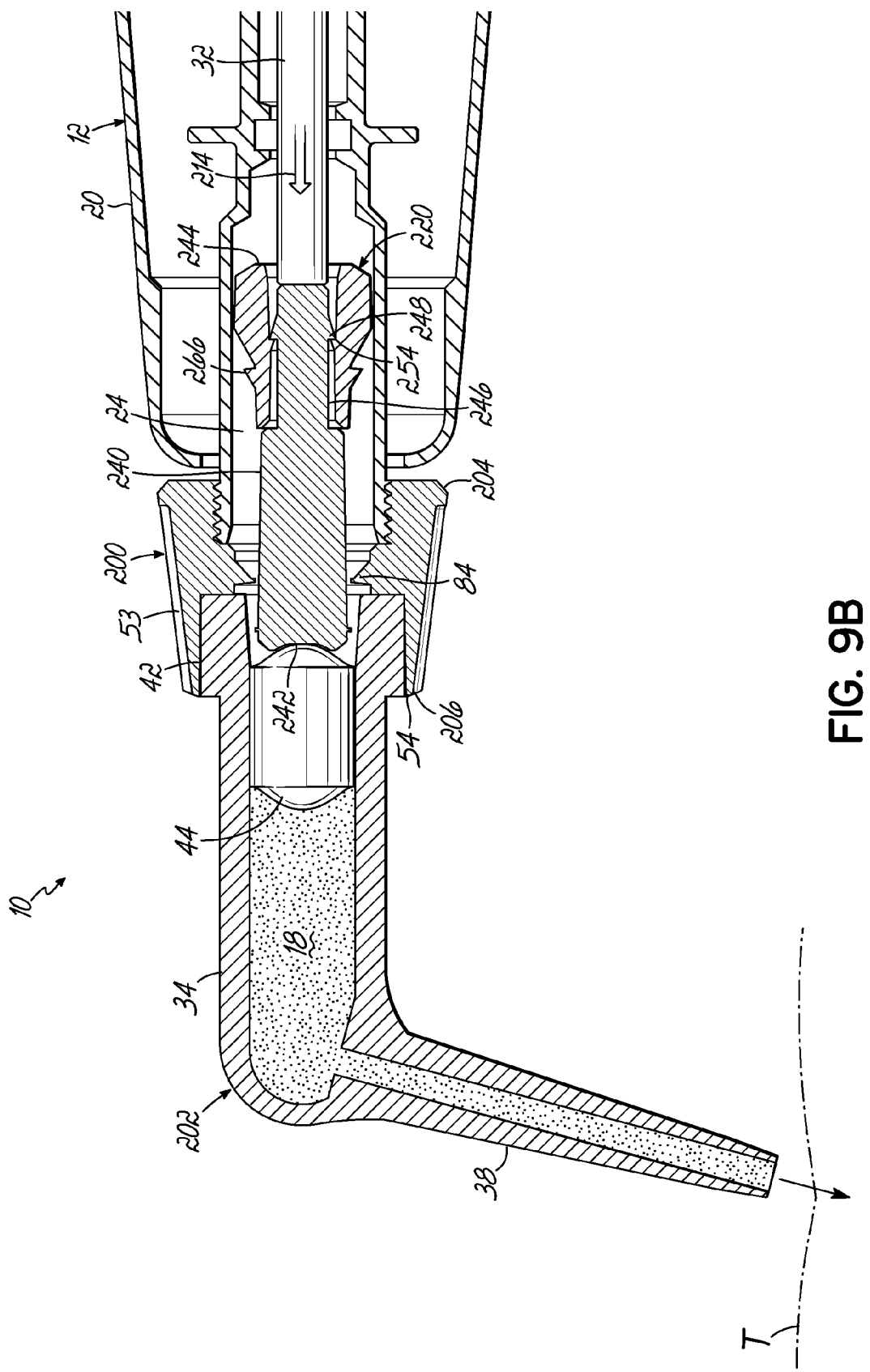
FIGS. 9B-9D are cross-sectional views of the dental instrument shown in FIG. 9A during dispensing of the dental material.
Figure 9C:
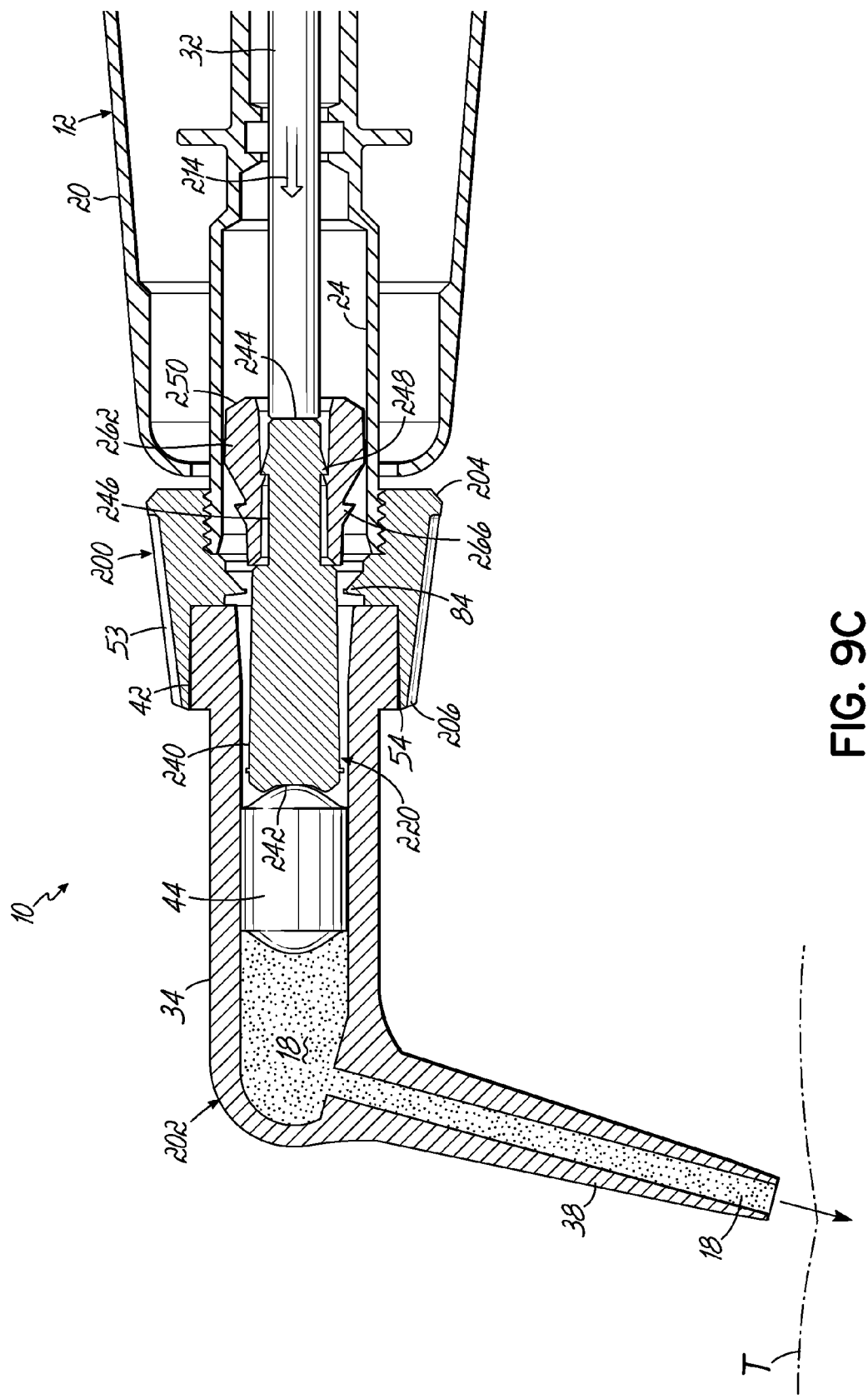

Following assembly of the adapter 200 with the handpiece 12, as is indicated in FIG. 9A, the dental material 18 may be discharged from the compule 202. With reference to FIGS. 9B and 9C, during use, the breakable tab 238 is configured to break at a predetermined load so that the plunger portion 220 separates from the coupling portion 204. As is described above, the breakable tab 238 fails at a location at or near the surface of the main body 240 so as to create a surface that may be flush or nearly flush with the surrounding surface of the main body 240 during use of cartridge 202. In particular, the instrument 10 may be brought into close proximity to a tooth T and the dental material 18 may be dispensed from the compule 202 by activating the energy source via the handpiece 12. At a predetermined threshold level of load, the breakable tab 238 fails. Failure of the tab 238 allows the plunger portion 220 to separate from the coupling portion 204 and drive the piston 44 generally in the direction indicated by arrow 214 as determined by the piston 32.

Once the breakable tab 238 fails, the plunger 220 may be moved relative to the coupling portion 204. As shown, the plunger 220 may then be pushed toward and then through the opening 54 to engage the piston 44. With further activation of the piston 32 in the direction of the arrow 214, together with any ultrasonic energy supplied by the handpiece 12, the plunger 220 is forced into the compule 202. The dental material 18 is thereby forced from the main body portion 34 and extruded out of the cannula 38 at the location on the tooth T. In one embodiment, the triangular shaped projection 84 may slidably cooperate with the exterior surface of the plunger 220 and may essentially seal the handpiece 12 from exposure to any dental material 18 that is squeezed backward between the piston 44 and the main body portion 34 during dispensing as is described above. In addition, or as an alternative, the skirt 262 may seal the plunger 220 from the remainder of the handpiece 12 and may also clean the receiving hole 24 of the handpiece 12 during extrusion of the dental material 18 from the cartridge 202.

Figure 9D:
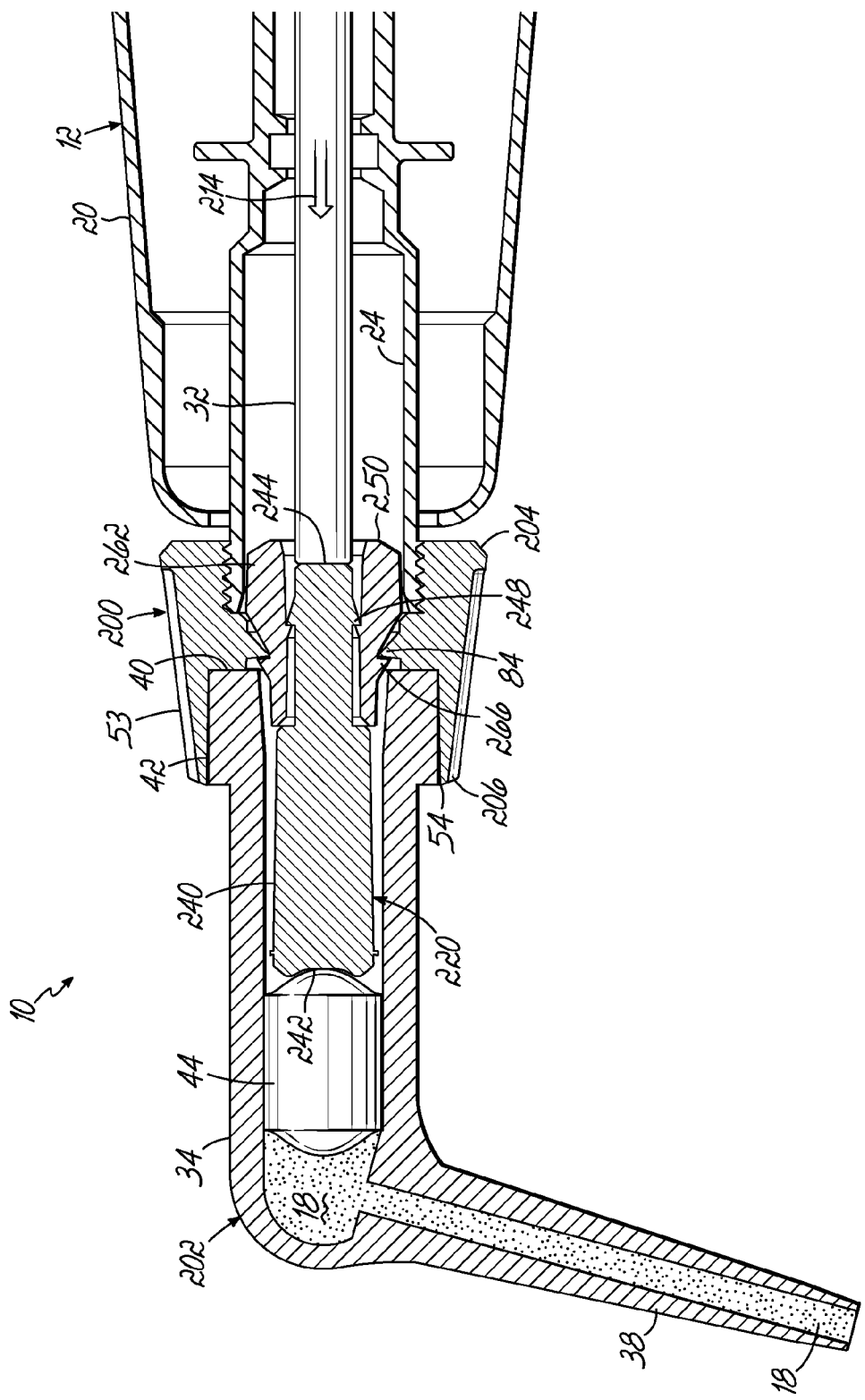

With continued reference to FIGS. 9C and 9D, as the piston 44 is pushed to near the end of the main body portion 34 proximate the cannula 38, the plunger 220 extends substantially into the main body portion 34 of the compule 202. At or near the end of the useful extension of the plunger 220, the ridge 266 on the plunger 220 may contact the projection 84 of the sidewall 206. With sufficient additional load on the plunger 220, the ridge 266 may push through an opening defined by the projection 84 (shown in FIG. 9D). The ridge 266 may then contact the flange 40 of the compule 202, at which position the plunger 220 may no longer be movable relative to the compule 202. The interference between the ridge 266 and the flange 40 may guarantee the usage of all the available stroke of the piston 32 of the handpiece 12 while preventing over stroke of the piston 32. As a result, dispensing of the dental material 18 from the compule 202 comes to a stop. Retraction of piston 32 into the handpiece 12 does not result in backwards movement of the plunger 220. In this regard, the interference fit between the ridge 266 and the triangular shaped projection 84 stops backwards movement of the plunger 220 within the adapter 200.

Once the clinician uses a desired amount of the dental material 18 from the compule 202 or the dental material 18 is substantially completely dispensed so as to push the ridge 266 through the opening defined by the triangular shaped projection 84, the clinician can disconnect the assembly of the compule 202 and the adapter 200 from the handpiece 12. The used compule and adapter may be then be disposed of. A new compule and adapter may be assembled with the handpiece 12 and the dental material within the new compule may be dispensed substantially the same way as described in the previous paragraphs.

Figure 10:
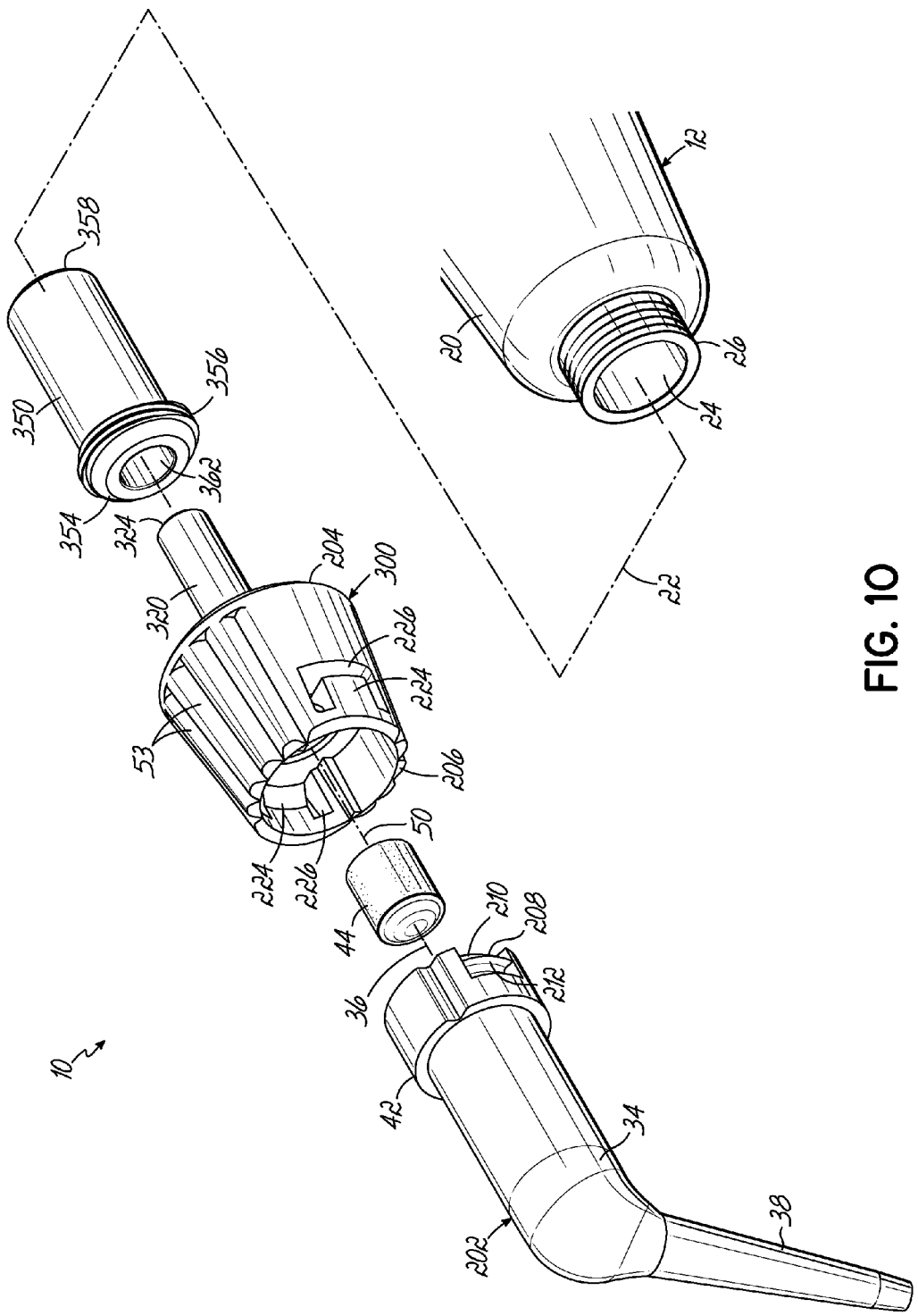
FIG. 10 is an exploded perspective view of a dental instrument according to one embodiment of the invention.
Figure 11A:
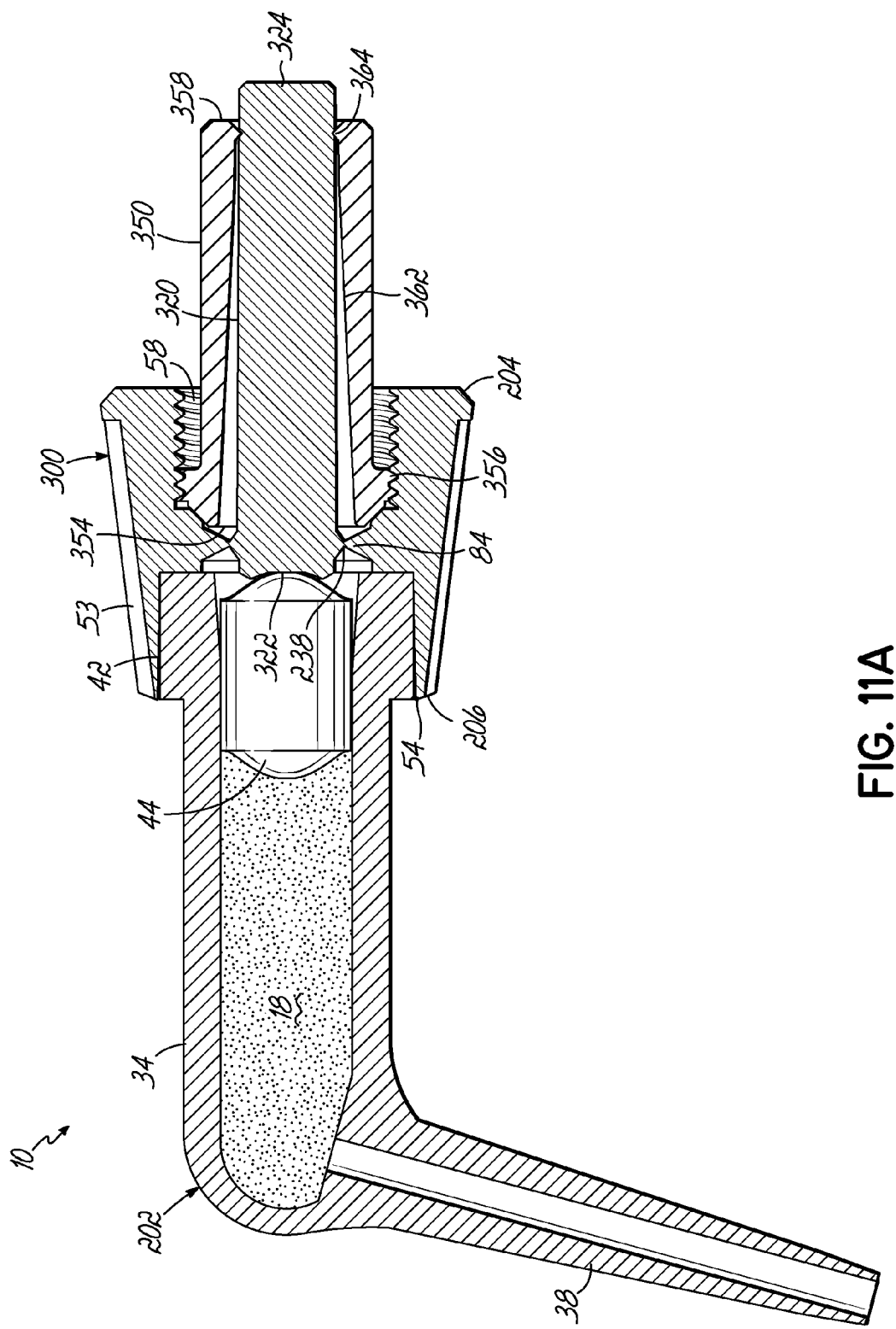
FIG. 11A is cross-sectional view of the compule assembled with the adapter shown in FIG. 10 prior to discharge of the dental material.
Figure 11B:
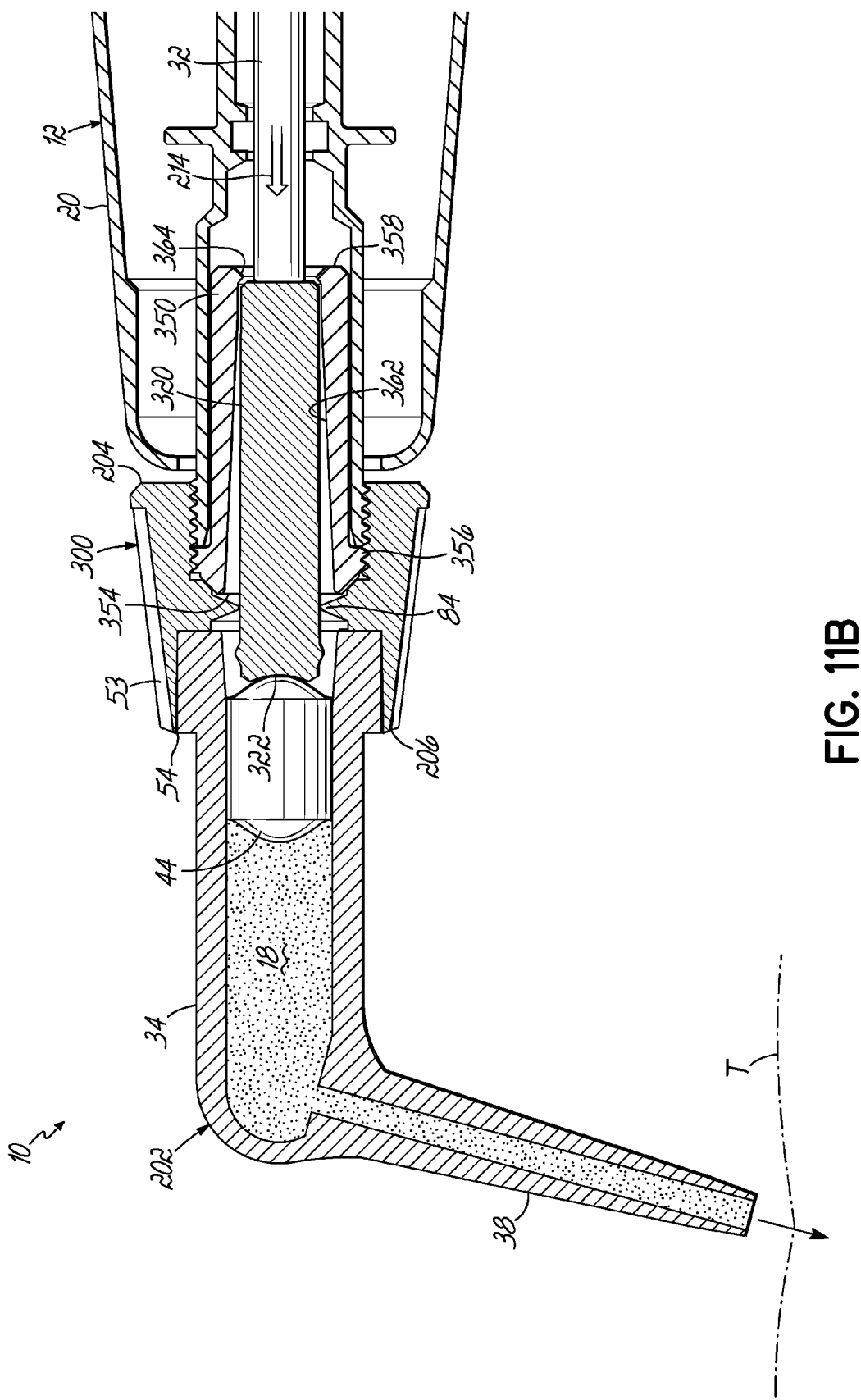
FIGS. 11B and 11C are cross-sectional views of the dental instrument shown in FIG. 11A during dispensing of the dental material.
Figure 11C:
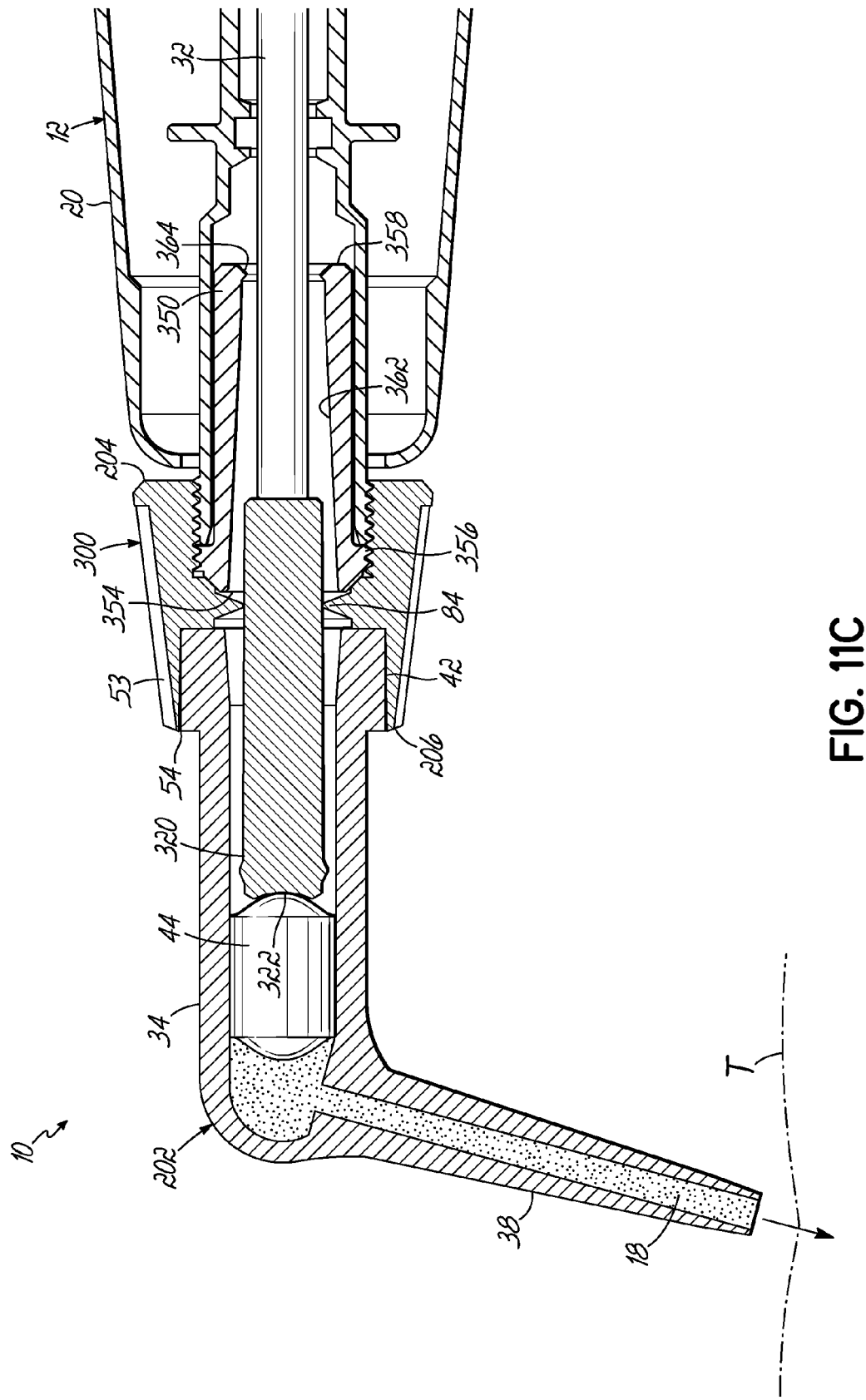
Figure 11D:
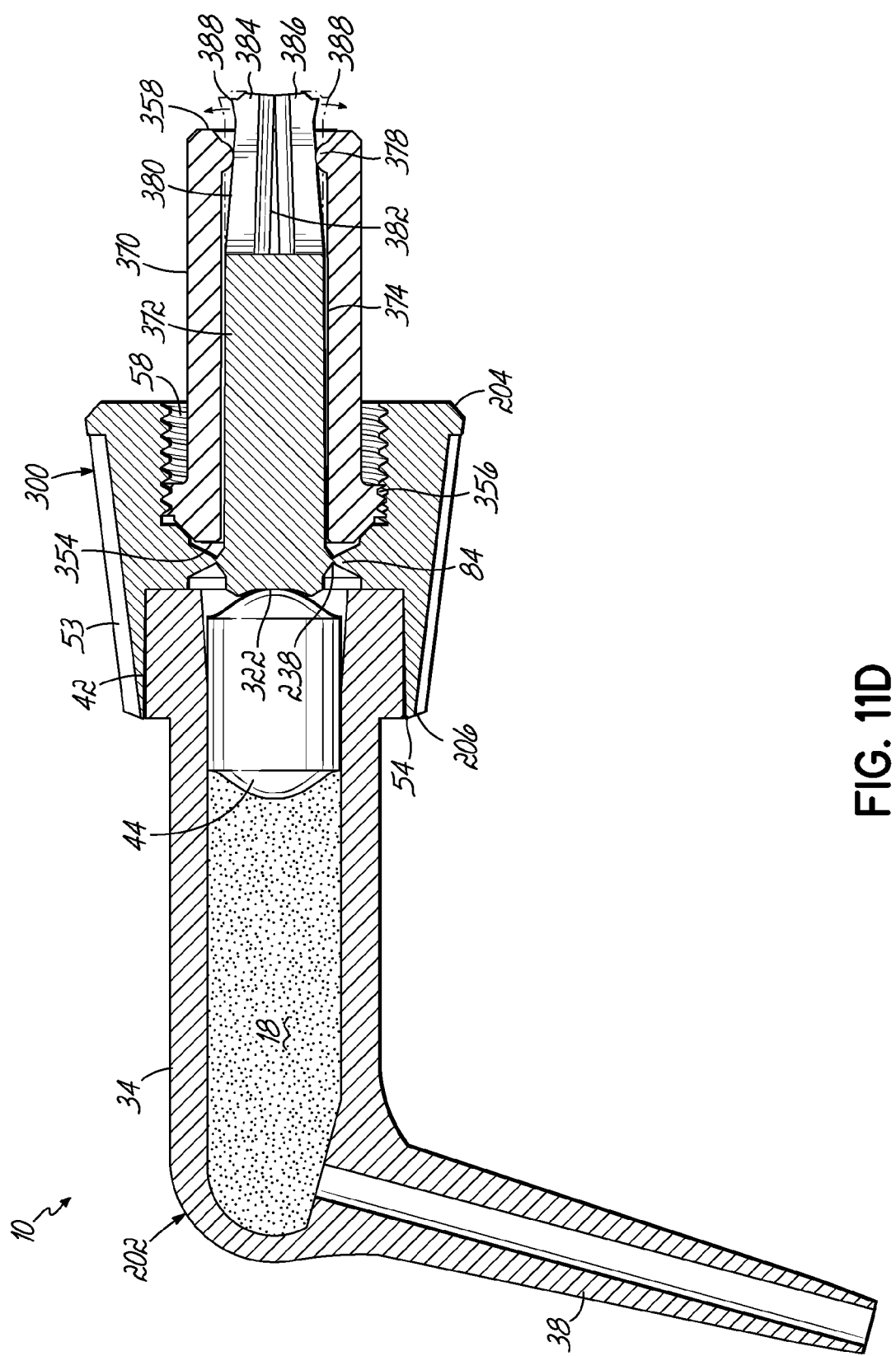
FIG. 11D is a cross-sectional view of a dental instrument according to one embodiment of the invention.

With reference now to FIGS. 10-11C, in which like reference numerals refer to like features throughout the figures, and in accordance with one embodiment of the invention, the dental instrument 10 may include an adapter 300 that couples the cartridge 202 to the handpiece 12. The adapter 300 differs from the adapter 200 shown in FIGS. 7-9D and described above. The adapter 300 further includes a plunger portion 320 that is received in the receiving hole 24 of the handpiece 12 to engage the piston 32 of the handpiece 12 and the piston 44 of the compule 202 during use, as is described below.

With reference to FIGS. 10 and 11A, in one embodiment, the plunger portion 320 is similar to the plunger 70 described above with reference to FIG. 2A. The plunger portion 320 is coupled to the coupling portion 204 by the breakable tab 238. The breakable tab 238 operates in a similar manner as the breakable tab 78, described above. The plunger portion 320 may be a generally cylindrical body extending along the longitudinal axis 50 from within the opening 58 of the coupling portion 204. The plunger portion 320 includes a leading or front surface 322 and a trailing surface 324. The front surface 322 is configured to cooperate with the piston 44 of the compule 202, and the trailing surface 324 cooperates with the piston 32 of the handpiece 12 to transfer movement of the piston 32 to the piston 44.

In the exemplary embodiment shown, the adapter 300 includes a shield member 350. The shield member 350 may be a separate component that is secured to the coupling portion 204. As shown, the shield member 350 may be a tubular member that is coupled to the coupling portion 204 at one end 354 and is generally concentric with the plunger portion 320 along the axis 50 toward an opposing end 358. By way of example only, and not limitation, the end 354 of the shield member 350 may include a thread 356 which may cooperate with a thread within the opening 58 of the coupling portion 204.

In one embodiment, the shield member 350 may define a tapered, cone-like bore 362 that is sized to receive the plunger portion 320. As shown, the bore 362 has a truncated cone configuration and, in the exemplary embodiment, is defined by a tapered side wall. Thus, while the outside dimension is substantially uniform, the inside dimension varies from a wide dimension at one end to a narrow dimension at the other end. The widest dimension of the bore 362 is adjacent the coupling portion 204 when the shield member 350 is coupled to the coupling portion 204. The bore 362 may include a rib 364 that may project inwardly toward the longitudinal axis 50 near the opposing end 358 of the shield member 350. In the exemplary embodiment shown, the opposing end 358 may define a bore that is slightly undersized relative to the plunger portion 320 when the shield member 350 is coupled to the coupling portion 204. The rib 364 may define a dimension that is less than the outside dimension of the plunger portion 320 at a location adjacent the shield member 350 when assembled. As result, assembly may result in the end 358 of the shield member 350 being in an expanded state with the rib 364 compressed against the outside diameter of the plunger portion 320 in the configuration shown in FIG. 11A.

Once secured within the opening 58 of the coupling portion 204, the shield member 350 may encircle the plunger portion 320 along nearly the entire length of the plunger portion 320. As shown in FIG. 11A, a short portion, including the trailing surface 324, of the plunger portion 320 may extend beyond the opposing end 358. In one embodiment, as is described in more detail below, the portion of the plunger portion 320 that extends beyond the end 358 of the shield member 350 may be approximately 10% of the total length of the plunger portion 320.

With reference now to FIG. 11B, when assembled, the shield member 350 is inserted within the receiving hole 24 of the handpiece 12. The end 26 of the handpiece 12 is coupled to the coupling portion 204 of the adapter 300. The cartridge 202 may be inserted into the opening 54 defined by the sidewall 206 as described above with reference to FIG. 7.

With continued reference to FIG. 11B, during use, activating the handpiece 12 extends the piston 32 into contact with the trailing surface 324 of the plunger portion 320. At some minimum threshold force, the breakable tab 238 (shown in FIG. 11A) fails and the plunger portion 320 separates from the coupling portion 204, as is described above.

With reference now to FIG. 11B, once the breakable tab 238 fails, the plunger 320 may be moved relative to the coupling portion 204. As shown, the plunger 320 may then be pushed through the opening 54 to engage the piston 44. The dental material 18 is thereby forced from the main body portion 34 and extruded out of the cannula 38 at the location on the tooth T. As the plunger portion 320 moves axially along the axis 50 to the position shown in FIG. 11B, it may be supported at two locations. The plunger portion 320 may be supported by the projection 84 and at the rib 364. Advantageously, because the plunger portion 320 is more fully supported, such as, at two axially spaced-apart locations, it is more likely to remain aligned with the cartridge 202 and is less likely to bend, tilt relative to the piston 44, or break during use of the adapter 300 during the initial extrusion of the dental material 18.

Once the plunger portion 320 moves axially to a position such as that shown in FIG. 11C, in which the trailing surface 324 is moved axially within the bore 362 and out of engagement with the rib 364, the plunger portion 320 may be prevented from reverting to its original position shown in FIG. 11A. In this regard, once the trailing surface 324 passes the rib 364, the shield member 350 may contract to a relaxed, unbiased condition. In the relaxed condition, the inside dimension of the bore 362 at the end 358, particularly at the rib 364, is less than the outside dimension of the plunger portion 320. Thus, the opening at the end 358 of the shield member 350 may slightly close. This configuration produces an interference fit between the plunger portion 320 and the shield member 350.

Any force on the plunger portion 320 pushing it backwards toward its starting position must be sufficient to expand the shield member 350. As such, the shield member 350 resists and possibly eliminates backwards movement of the plunger portion 320 once it reaches a predetermined axial location. In the exemplary embodiment, once the plunger portion 320 is pushed axially to at least 10% of its total stroke toward the compule 202, which may be at or slightly past the rib 364, the plunger portion 320 is locked from being pushed backward toward its original position. In one embodiment, once the clinician uses at least about 10% of the dental material 18, the plunger portion 320 may no longer be visible and may only be accessible with the piston 32 of the handpiece 12.

In one embodiment, the shield member 350 may contain any dental material 18 that is squeezed backward and penetrates between the projection 84 and the plunger portion 320. The dental material 18 may therefore be contained within the bore 362 and not contact the dental handpiece 12.

In one embodiment, as is shown in FIG. 11C, as the piston 44 is pushed to near the end of the main body portion 34 proximate the cannula 38, the plunger 320 extends substantially into the main body portion 34 of the compule 202 at or near the end of the useful extension of the plunger 320. Although not shown in the FIG. 11C, the plunger 320 may include a projection or other feature similar to the rib 266 or the ridge 79 that couples with a projection on the coupling portion 204 to retain the plunger 320 at or near the end of its useful stroke.

In one embodiment, a shield member 370 and a plunger portion 372 are different from those shown in FIGS. 11A-11C. In particular, with reference to FIG. 11D, the shield member 370 is a tubular member having substantially parallel inner and outer sidewalls. Thus, the shield member 370 is substantially uniformly thick, whereas the shield member 350 is tapered. The shield member 370 defines a bore 374 that is substantially uniformly formed so as to be a right circular cylinder. A projection or ridge 378 projects radially inwardly to define a reduced diameter at or near the end 358.

The ridge 378 engages the plunger portion 372 prior to and during use of the adapter 300.

The plunger portion 372 differs from the plunger portion 320 shown in FIG. 11A. With regard to the differences, the plunger portion 372 includes a split end 380 having slot 382. The slot 382 defines opposing portions 384, 386. The opposing portions 384, 386 may be biased outwardly. So, in the position shown, the portions 384, 386 may be elastically deformed inwardly by the ridge 378 with an unbiased position shown in phantom line. The slot 382 may be a single side-to-side slot or have a cruciform configuration, which would define four opposing portions or quarters. In the exemplary embodiment shown, the split end 380 includes a stop 388 on each portion 384, 386. The stops 388 may have a saw-tooth like configuration. As shown, the end 380 is at least partially exposed from within the shield member 370 with the split end 380 being compressed by engagement with the ridge 378. That is, each of the portions 384, 386 may be in contact with one another or the portions 384, 386 may be only slightly spaced apart from one another. The plunger portion 372 is initially coupled to the coupling portion 204 by the breakable tab 238.

During dispensing, the piston (not shown in FIG. 11D) contacts and pushes on the split end 380 until the breakable tab 238 breaks, as is described above, and the plunger portion 372 is moved axially relative to the shield member 370. Once the split end 380 slides past the ridge 378, the split end 380 expands. In other words, the portions 384, 386 may spring outwardly away from one another and may contact the bore 374. Once the portions 384, 386 spring outwardly, the stops 388 are positioned in an interfering relationship with the ridge 378. Any movement of the plunger portion 372 backwards is resisted by the interference fit between the stops 388 and the ridge 378.

At or near the end of dispensing of the dental material and when the plunger portion 372 reaches the end of its full stroke, the stops 388 may engage and push through the projection 84. The stops 388 may then lock the plunger portion 372 at or near its extended position. This configuration may be similar to that shown in FIG. 3C between the ridge 79 and the projection 84.

Once the dental material 18 is substantially completely dispensed, the clinician can disconnect the compule and adapter from the handpiece 12. The used compule and adapter may then be discarded. A new compule and adapter may be assembled with the handpiece 12 and the dental material within the new compule may be dispensed substantially the same way as described in the previous paragraphs.

Figure 12:
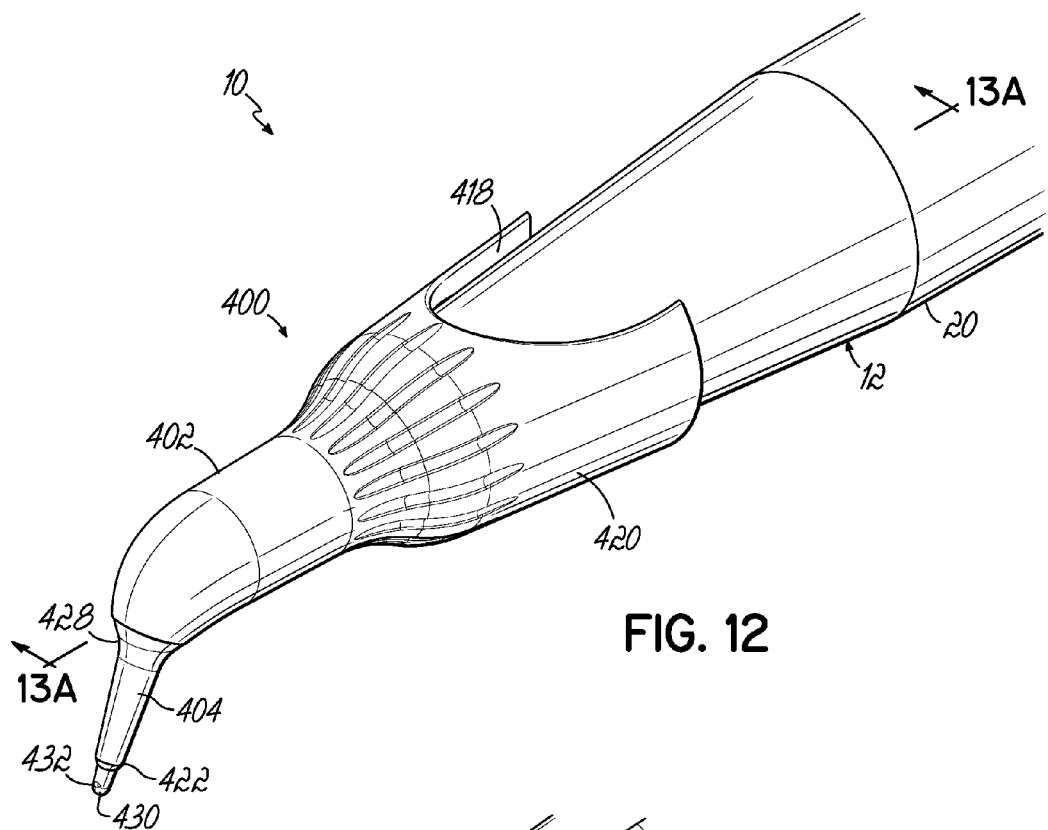
FIG. 12 is a perspective view of a dental instrument according to one embodiment of the invention.
Figure 13B:
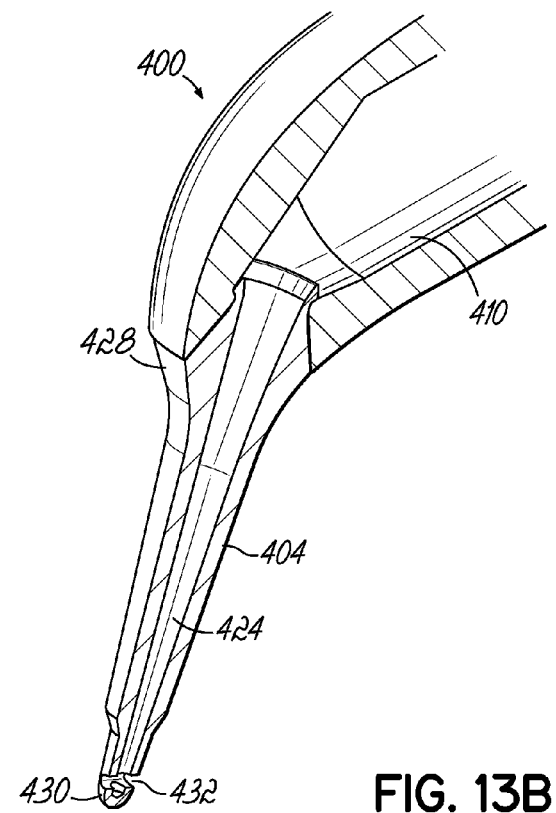
FIG. 13B is an enlarged view of the tip shown in FIG. 13B.
Figure 13A:
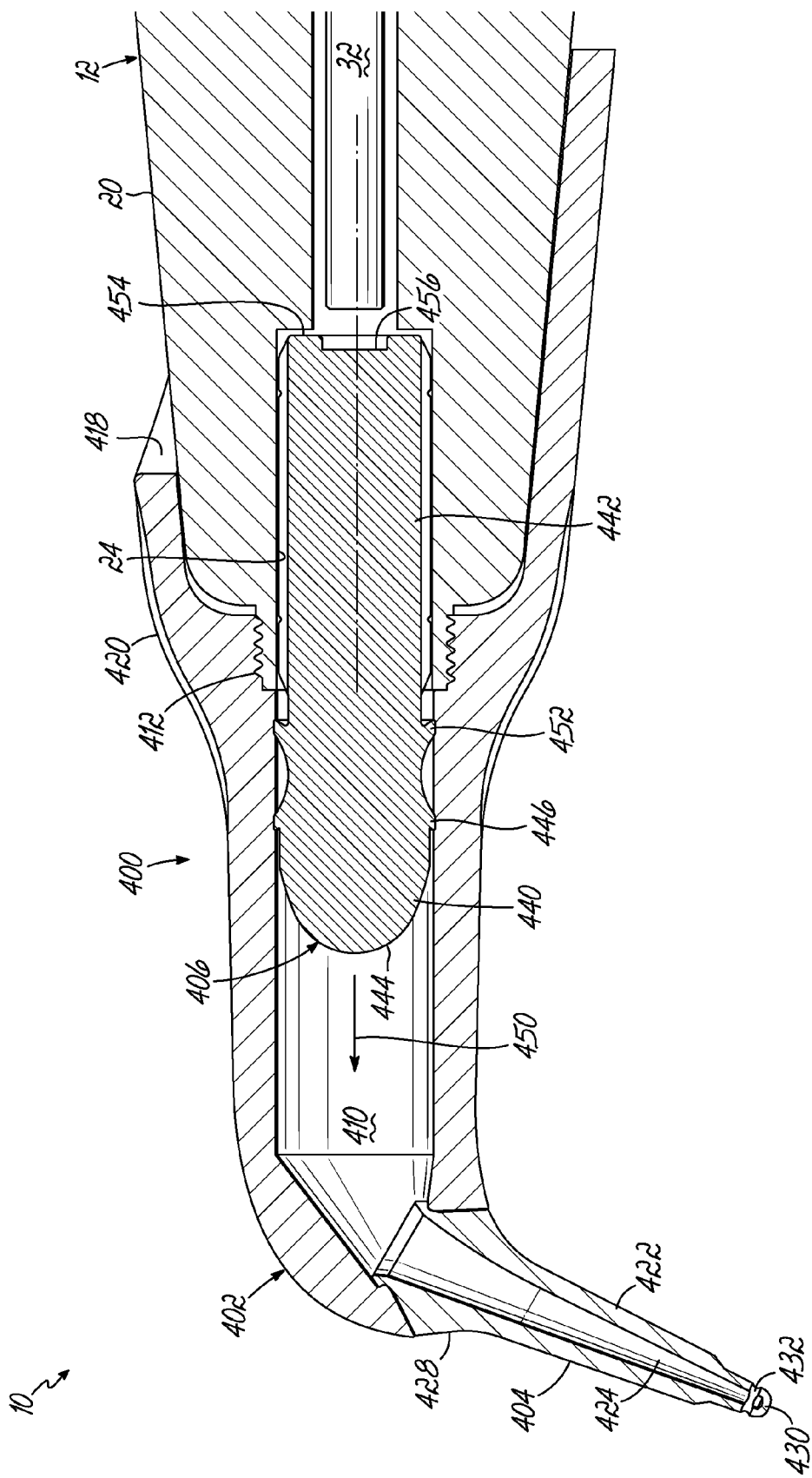
FIG. 13A is a cross-sectional view of the dental instrument shown in FIG. 12 taken along section line 13A-13A.

With reference now to FIGS. 12, 13A, and 13B, in accordance with one embodiment of the invention, a tip 400 may contain a dental material. In this embodiment, no adapter may be utilized. The tip 400 may be configured specifically for a particular make and model of the handpiece 12 (e.g., the Sonicfill® handpiece). As with the adapters described above with reference to FIGS. 1-13D, the tip 400 may be a consumable in that it may be used only a single time and then be discarded. The tip 400 may include a main housing 402 within which the dental material is stored prior to use and a needle 404 that extends from the housing 402 for directing the dental material from the main housing 402 to the point of use. With reference to FIG. 13A, the tip 400 also includes a plunger 406 that contacts the piston 32 of the handpiece 12 at one end and is slidably received in the main housing 402. Movement of the plunger 406 into the housing 402 extrudes dental material from the needle 404.

To these and other ends, and with reference to FIGS. 12, 13A, and 13B, the housing 402 is a tubular member and defines a chamber 410. Although not shown, the chamber 410 may be filled with one of a variety of dental materials and may further contain a portion of the plunger 406. The chamber 410 may also define a thread 412, which is sized so that the tip 400 may be secured to the thread at the end 26 of the handpiece 12. As shown, in the exemplary embodiment, the main housing 402 wraps over an end portion of the shaft 20 of the handpiece 12 with a shroud 420. The shroud 420 may conform to the shaft 20, as shown, but embodiments of the present invention are not limited to any conformity of the housing 402 to the shaft 20. Advantageously, the shroud 420 protects the handpiece 12 from inadvertent contact with the patient's secretions and teeth as well as prevents accidental contact of the handpiece 12 with dental material. The shroud 420 may include a cutout or notch 418, which may facilitate removal of the tip 400 from the handpiece 12.

With reference to FIG. 13B, the needle 404 includes a shaft 422 that is coupled to the housing 402 by a hub 428. The shaft 422 and the hub 428 define a lumen 424. The chamber 410 and the lumen 424 are open to one another so that lumen 424 directs the dental material from the chamber 410 to a predetermined location in the patient's mouth upon activation of the plunger 406.

In the exemplary embodiment shown in FIG. 13B, the needle 404 has a point 430 that defines at least one opening 432 at which location the dental material may be discharged from the tip 400. The opening 432 may be referred to as an eye herein and may be oriented substantially perpendicular to the lumen 424, the dental material being dispensed from the point 430 in a direction perpendicular to the lumen 424. In the exemplary embodiment shown, the point 430 includes two eyes 432 oriented in opposing directions in the point 430. The dental material therefore may exit the point 430 radially from a longitudinal axis defined by the needle 404.

With reference now to FIG. 13A, the plunger 406 is a generally cylindrical body having a torpedo-like configuration with a head portion 440 and a tail portion 442. The head portion 440 is positioned in the chamber 410 of the housing 402. It will be appreciated that the head portion 440 may be directly in contact with the dental material (not shown) during use of the tip 400.

As shown, the head portion 440 may include a rounded to cone-like leading surface 444 that transitions to an annular leading rib 446. The rib 446 contacts the wall defining the chamber 410 and may form a seal between the head portion 440 and the tail portion 442 of the plunger 406. During use, as the plunger 406 is forced in the direction indicated by arrow 450, the rib 446 may slide along the wall of the chamber 410 to push the dental material toward the needle 404.

The plunger 406 may further include a secondary rib 452 axially spaced apart from the rib 446. As with the rib 446, the secondary rib 452 may form a sliding seal between the plunger 406 and the housing 402. As a result, one or both ribs 446, 452 of the plunger 406 may resist back flow of the dental material during extrusion from the needle 404. Thus, the ribs 446, 452 may sealingly engage the housing 402 so as to prevent contact between the dental material 18 and handpiece 12, which may prolong the useful lifetime of handpiece 12 by at least limiting corrosion of the handpiece 12, particularly the metal components, as well as reduce the time required to clean any residue of the dental material 18 from the handpiece 12. As is disclosed herein, embodiments of the tip may advantageously form a barrier between the dental material and the handpiece and thus reduce or completely eliminate contact between the two. That is, no portion of the handpiece 12, including the piston 32, may come into contact with dental material. Another advantage may be that this configuration may provide a barrier between the handpiece 12 and the patient and thus reduce the risk of the patient being infected with an iatrogenic disease should the clinician fail to adequately disinfect the handpiece 12 between uses.

With continued reference to FIG. 13A, the tail portion 442 includes a trailing surface 454 in which a pocket 456 may be formed. As shown, the pocket 456 cooperates with the piston 32 of the handpiece 12. The tail portion 442 of the plunger 406 is inserted into the receiving hole 24 of the handpiece 12 during installation of the tip 400.

Figure 13C:
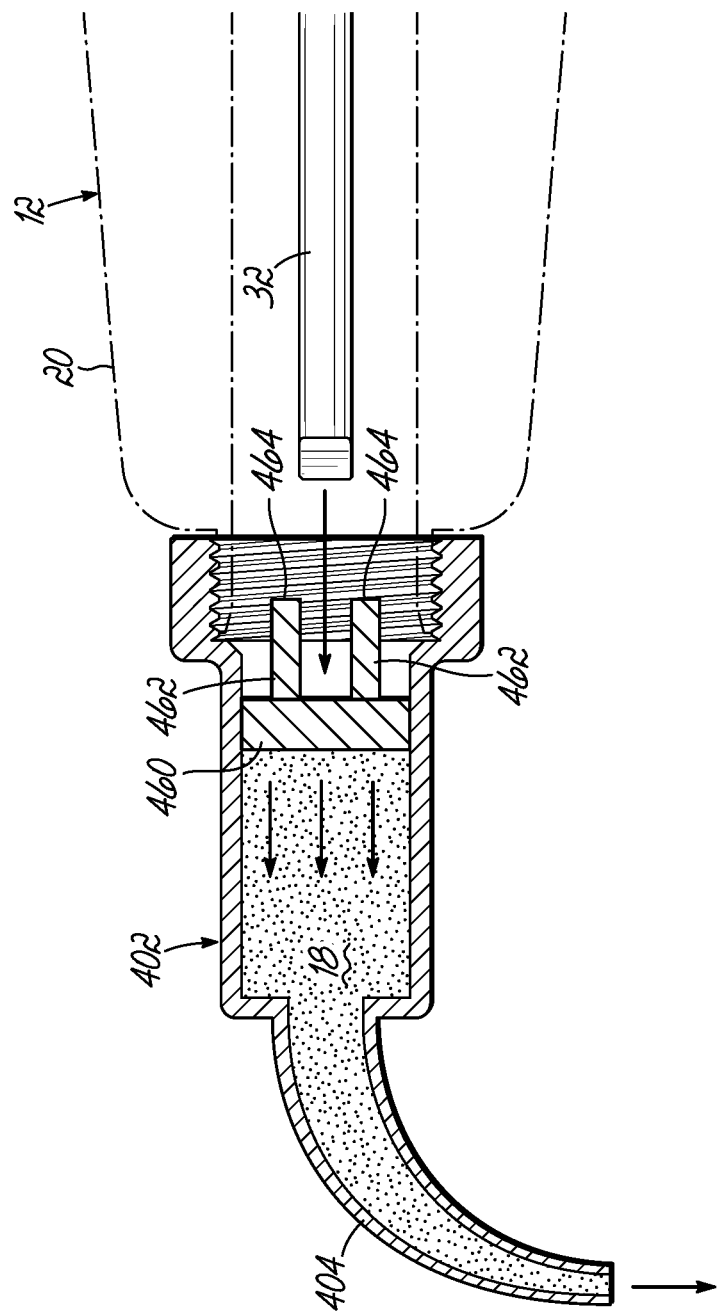
FIG. 13C is a cross-sectional view of a tip according to one embodiment of the invention.

As is shown in FIG. 13C, in an alternative embodiment, a plunger 460 has a generally planar configuration in contact with the dental material 18 and is movable within the housing 402. As with previous embodiments, the plunger 460 moves relative to the housing 402 to force the dental material through the needle 404. The plunger 460 includes a tab 462 with wings 464 on one side of the plunger 460 opposite the dental material 18. The wings 464 are spaced apart to receive the piston 32. During use, the tab 462 encircles the piston 32 and generally has at least two functions.

According to one embodiment, the tab 462 receives the piston 32 and substantially prevents the plunger 460 from tilting relative to the piston 32. In this way, the plunger 460 is maintained at a generally perpendicular orientation relative to the piston 32. It will be appreciated that the plunger 460 is therefore more likely to stay engaged within the housing 402 along a peripheral edge of the plunger 460 and is correspondingly less likely to allow dental material to leak between the peripheral edge of the plunger 460 and the housing 402.

And, according to a second function, the tab 462 shields the piston 32 from any dental material 18 that does leak between the plunger 460 and the housing 402. In this regard, the tab 462 prevents issues with corrosion of the piston 32 and advantageously maintains the cleanliness of the handpiece 12.

Figure 14:
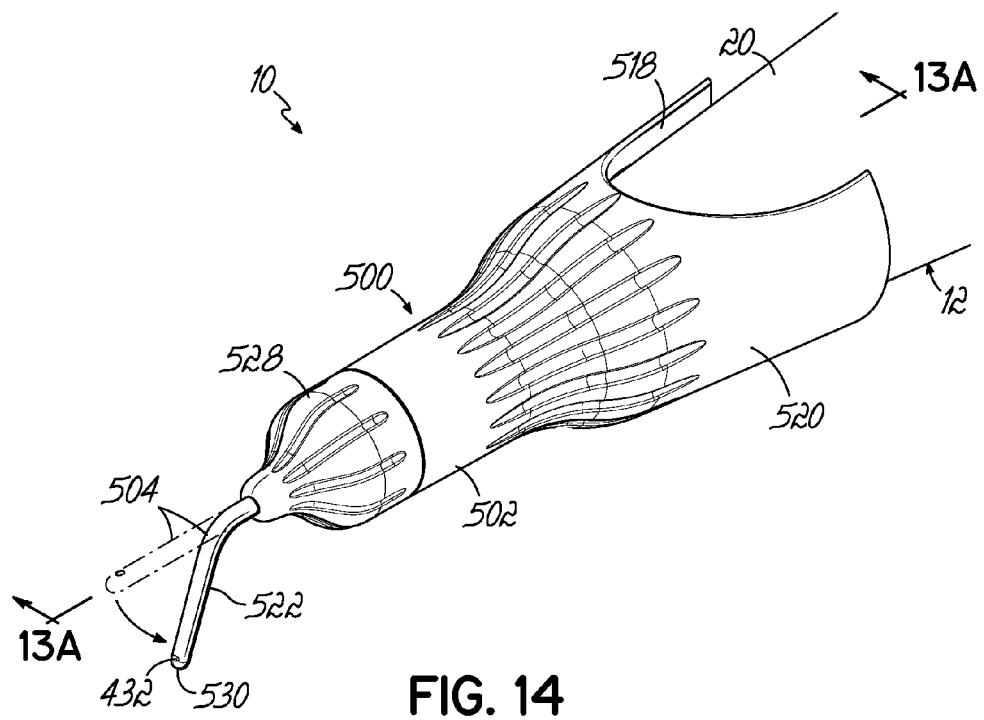
FIG. 14 is a perspective view of a dental instrument according to one embodiment of the invention.
Figure 15:
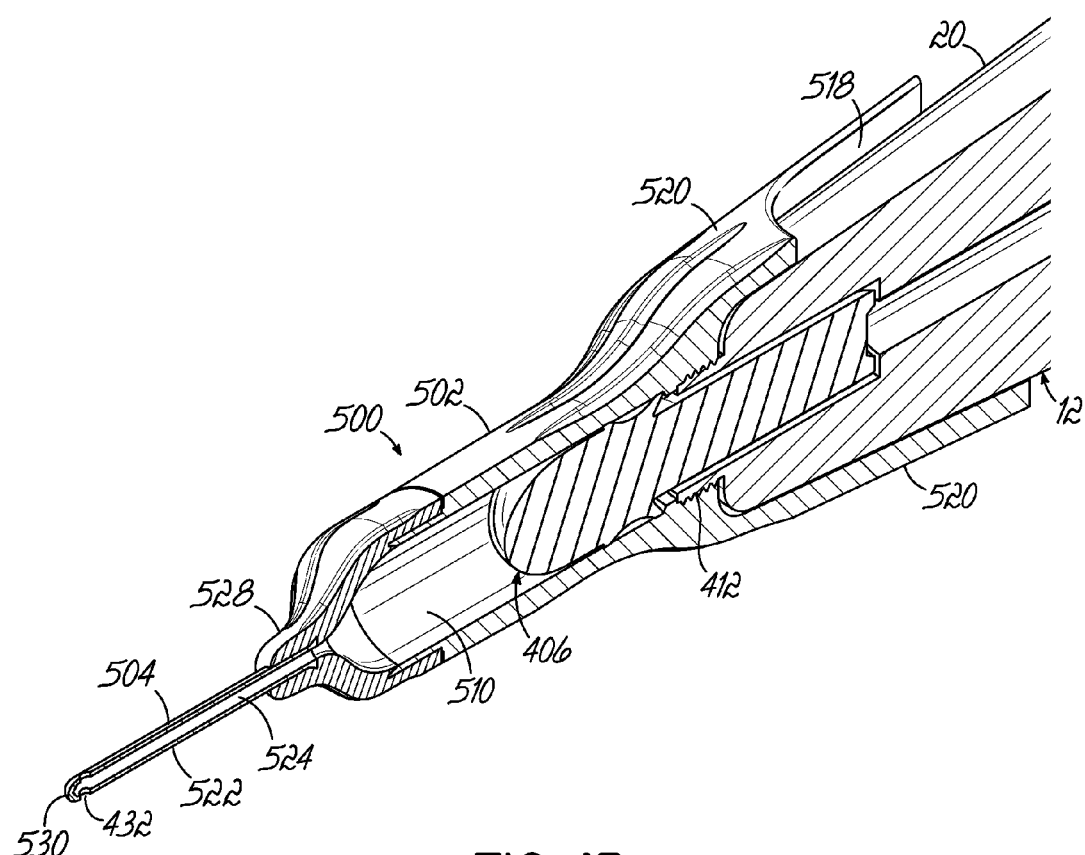
FIG. 15 is a cross-sectional view of the dental instrument shown in FIG. 14 taken along section line 15-15.

Referring to FIGS. 14 and 15, in accordance with one embodiment of the invention in which like reference numerals refer to like features of FIGS. 12-13B, a tip 500 may contain a dental material and be coupled to the handpiece 12 in a similar manner to the tip 400 shown in FIGS. 12-13B. The tip 500 may include a main housing 502 within which the dental material is stored prior to use and a needle 504 that extends from the housing 502 for directing the dental material from the main housing 502 to the point of use. The tip 500 may also include the plunger 406 that contacts the piston 32 of the handpiece 12 at one end and is slidably received in the main housing 502. Movement of the plunger 406 into the housing 502 extrudes dental material from the needle 504.

To these and other ends, and with reference to FIGS. 14 and 15, the housing 502 is a tubular member and defines a chamber 510, which may be filled with one of a variety of dental materials and may further contain a portion of the plunger 406. The chamber 510 may also define the thread 412, which is sized so that the tip 500 may be secured to the thread at the end 26 of the handpiece 12. As shown, in the exemplary embodiment, the main housing 502 wraps over an end portion of the shaft 20 of the handpiece 12 with a shroud 520. The shroud 520 may conform to the shaft 20, as shown, but embodiments of the present invention are not limited to any conformity of the housing 502 to the shaft 20. Advantageously, the shroud 520 protects the handpiece 12 from inadvertent contact with the patient's secretions and teeth as well as prevents accidental contact of the handpiece 12 with dental material. The shroud 520 may define a notch 518 which may facilitate removal of the tip 500 from the dental handpiece 12.

With reference to FIG. 15, the needle 504 includes a shaft 522 that is coupled to the housing 502 by a hub 528. The shaft 522 and a portion of the hub 528 define a lumen 524. The chamber 510 and the lumen 524 are open to one another so that lumen 524 directs the dental material from the chamber 510 to a predetermined location in the patient's mouth upon activation of the plunger 406. In the exemplary embodiment, the needle 504, particularly the shaft 522, is deformable along its longitudinal axis, as is indicated by phantom line in FIG. 14. That is, the clinician may bend the shaft 522 to one or more orientations and the shaft 522 will remain in the selected orientation. By way of example only, and not limitation, the shaft 522 may be bent to the position shown in FIG. 14 or to another selected position including one in which the lumen 524 is generally concentric with the chamber 510 as is shown in FIG. 15.

With continued reference to FIG. 15, the needle 504 has a point 530 that defines at least one eye 432 at which location the dental material may be discharged from the tip 500. In the exemplary embodiment, the point 530 includes two eyes 432 oriented in opposing directions in the point 530. The dental material exits the point 530 radially from the needle 504.

Figure 16:
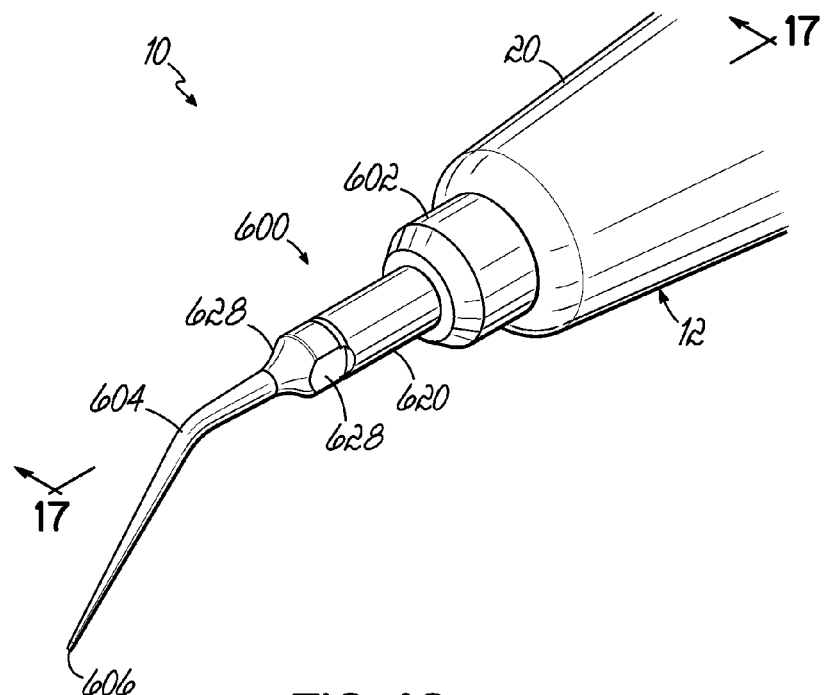
FIG. 16 is a perspective view of a dental instrument according to one embodiment of the invention.
Figure 17:
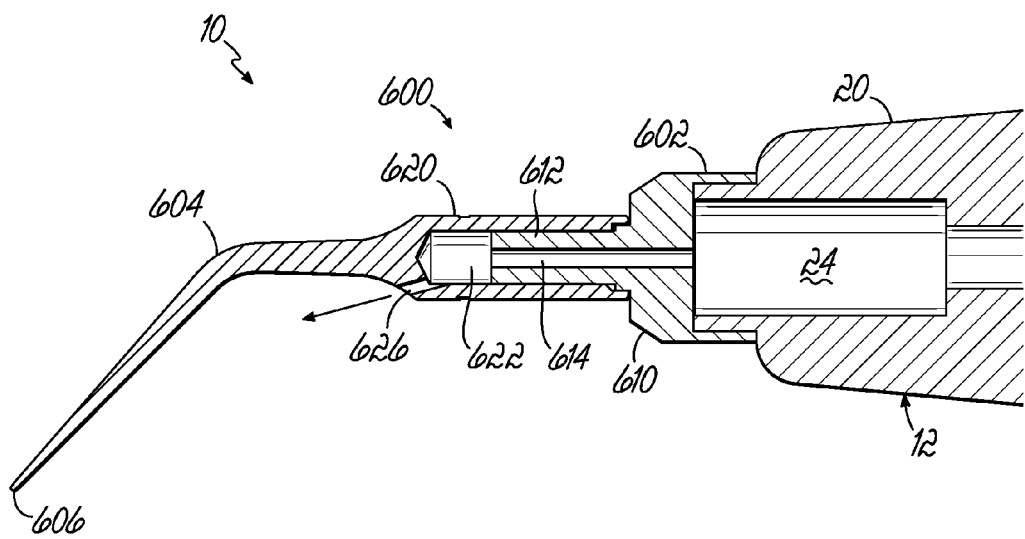
FIG. 17 is a cross-sectional view of the dental instrument shown in FIG. 16 taken along section line 17-17.

With reference now to FIGS. 16 and 17, in accordance with one embodiment of the invention in which like reference numerals refer to like features throughout the figures, a tip 600 may be coupled to the handpiece 12 by a threaded connection or by other means. The tip 600 may transmit vibrations, such as, sonic or ultrasonic vibrations from the handpiece 12 to a controlled, well defined location. To that end, the tip 600 may include a hub 602 that couples a probe 604 to the handpiece 12. Vibrations from the handpiece 12 may then be transmitted to the probe 604. A clinician may then specifically direct the vibrations to a relatively localized region in or on the patient's tooth.

In the exemplary embodiment, the hub 602 may function as an adapter between the probe 604 and the handpiece 12. In that regard, the hub 602 may include a main body 610 from which extends a stud 612. As shown, the stud 612 may be smaller in diameter than the main body 610 and extend concentrically from the main body 610. The main body 610 includes a through bore 614 that communicates with the receiving hole 24 of the handpiece 12.

The probe 604 may be a solid needle-like member ending in a point 606 and may have a doglegged or another non-linear configuration. The probe 604 may lack a lumen and may not dispense a dental material. The probe 604 may include a sleeve portion 620 that is slidably received on the stud 612. As shown, when the sleeve portion 620 is positioned on stud 612, a chamber 622 is defined between the stud 612 and the sleeve portion 620. The probe 604 may include a vent 626 that communicates with the chamber 622. The vent 626 may facilitate assembly by relieving any air pressure buildup within the chamber 622 as the probe 604, specifically the sleeve portion 620, is assembled on the stud 612. In a similar manner, the through bore 614 relieves pressure buildup as the hub 602 is assembled with the handpiece 12. As shown in FIG. 16, the probe 604 may include two flats 628 for receiving a tool, such as a wrench, for tightening the tip 600 on the handpiece 12. Once assembled with the handpiece 12, the clinician may position the point 606 against a specific location and transmit sonic energy to that location.

While the present invention has been illustrated by a description of various embodiments and while these embodiments have been described in some detail, it is not the intention of the inventors to restrict or in any way limit the scope of the appended claims to such detail. Thus, additional advantages and modifications will readily appear to those of ordinary skill in the art. The various features of the invention may be used alone or in any combination depending on the needs and preferences of the user.

What is claimed is:

1. An adapter for coupling a compule, which contains a dental material, with a dental handpiece that includes a piston, comprising:
   a coupling portion including a sidewall defining a first opening for selectively and removably attaching the adapter to the compule and a second opening for selectively and removably attaching the adapter to the dental handpiece;
   a plunger portion extending through the second opening of the coupling portion, the plunger portion engaging the piston during dispensing of the dental material; and
   a breakable tab connecting the coupling portion and the plunger portion, the breakable tab being configured to break at a minimum predetermined load during dispensing of the dental material,
   wherein when the breakable tab breaks, the plunger portion is movable relative to the coupling portion.

2. The adapter of claim 1 wherein the first opening is configured to prevent disassembly of the compule from the adapter once the compule is assembled with the adapter.

3. The adapter of claim 1 wherein the coupling portion and the plunger portion define a longitudinal axis of the adapter and the first opening is defined by a C-shaped sidewall so that the compule is coupled to the adapter in a direction that is perpendicular to the longitudinal axis.

4. The adapter of claim 3 wherein the C-shaped sidewall includes a first portion and a second portion defining a first transverse dimension and a second transverse dimension, respectively, relative to the longitudinal axis and at least one of the first and second transverse dimensions is less than an outside dimension of the compule.

5. The adapter of claim 1 wherein the coupling portion includes a bendable tab that is configured to engage the compule.

6. The adapter of claim 1 wherein the first opening includes a snap-fit connection or a snap-on connection.

7. The adapter of claim 1 wherein during dispensing the plunger portion locks the compule to the coupling portion.

8. The adapter of claim 1 wherein the sidewall includes a projection between the coupling portion and the plunger portion, and when the breakable tab breaks, the projection slidably engages the plunger portion during dispensing.

9. The adapter of claim 1 wherein the coupling portion forms a sliding seal with the plunger portion that substantially prevents contact between the dental material and the handpiece during dispensing.

10. The adapter of claim 1 wherein the breakable tab extends along an entire perimeter between the coupling portion and the plunger portion.

11. The adapter of claim 1 wherein the sidewall includes a projection and the breakable tab extends between the projection and the plunger portion.

12. The adapter of claim 11 wherein when the breakable tab breaks, the projection has a triangular shape.

13. The adapter of claim 11 wherein the plunger portion includes a ridge that engages the projection during dispensing to prevent the plunger portion from disengaging from the coupling portion at or near an end of dispensing of the dental material.

14. The adapter of claim 13 wherein the plunger portion includes a main body coupled to the coupling portion by the breakable tab and a sleeve that is slidable onto an end of the main body, and wherein the sleeve includes the ridge that engages the projection.

15. The adapter of claim 14 wherein the sleeve defines a skirt that is sized to slide in contact with the dental handpiece during dispensing of the dental material.

16. The adapter of claim 1 further including a shield member slidably received on the plunger portion and configured to cooperate with the coupling portion during dispensing to substantially prevent the dental material passing between the plunger portion and the coupling portion from contacting the dental handpiece.

17. The adapter of claim 16 wherein the shield member includes a truncated cone-shaped bore defining a narrow dimension and a wide dimension and the shield member is positioned on the plunger portion such that the wide dimension is adjacent the coupling portion.

18. The adapter of claim 16 wherein at least one of the shield member and the plunger portion is biased against the other of the shield member and the plunger portion prior to dispensing.

* * * * *